US011589425B2

(12) United States Patent
Hejazi et al.

(10) Patent No.: US 11,589,425 B2
(45) Date of Patent: Feb. 21, 2023

(54) SHAPE MEMORY MATERIAL FOR CONTROLLED LIQUID DELIVERY IN AN AEROSOL DELIVERY DEVICE

(71) Applicant: RAI STRATEGIC HOLDINGS, INC., Winston-Salem, NC (US)

(72) Inventors: Vahid Hejazi, Concord, NC (US); Stephen B. Sears, Siler City, NC (US); Eric T. Hunt, Pfafftown, NC (US); Karen V. Taluskie, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 935 days.

(21) Appl. No.: 16/422,338

(22) Filed: May 24, 2019

(65) Prior Publication Data

US 2020/0367572 A1 Nov. 26, 2020

(51) Int. Cl.
*H05B 3/12* (2006.01)
*A61M 11/04* (2006.01)
(Continued)

(52) U.S. Cl.
CPC ............. *H05B 3/12* (2013.01); *A61M 11/042* (2014.02); *A61M 15/0013* (2014.02);
(Continued)

(58) Field of Classification Search
CPC ..... A24F 40/10; A24F 40/485; A61M 11/042; A61M 15/0013; A61M 15/0028;
(Continued)

(56) References Cited

U.S. PATENT DOCUMENTS 2,057,353 A 10/1936 Whittemore, Jr.
2,104,266 A 1/1938 McCormick
(Continued)

FOREIGN PATENT DOCUMENTS

CN 1541577 A 11/2004
CN 2719043 Y 8/2005
(Continued)

OTHER PUBLICATIONS

International Search Report from the corresponding International Application No. PCT/IB2020/054802, dated Jul. 29, 2020.

*Primary Examiner* — Dana Ross
*Assistant Examiner* — Joe E Mills, Jr.
(74) *Attorney, Agent, or Firm* — Womble Bond Dickinson (US) LLP

(57) ABSTRACT

The present disclosure provides an aerosol delivery device and a cartridge for an aerosol delivery device. In various implementations, the cartridge may comprise a housing defining a liquid reservoir, an atomizer configured to produce an aerosol, the atomizer comprising a first liquid transport element, a second liquid transport element, and a microvalve located between the liquid reservoir and the second liquid transport element. The microvalve may comprise a base member including at least one channel, and an actuating member at least a portion of which comprises a shape-memory material, and which is configured to move between a first position and a second position, wherein in the first position, the actuating member substantially blocks fluid flow from the liquid reservoir through the channel, and in the second position, the actuating member allows fluid flow from the liquid reservoir through the channel and to the second liquid transport element.

36 Claims, 13 Drawing Sheets

(51) Int. Cl.
*A61M 15/00* (2006.01)
*A61M 15/06* (2006.01)

(52) U.S. Cl.
CPC ......... *A61M 15/0028* (2013.01); *A61M 15/06* (2013.01); *A61M 2205/13* (2013.01)

(58) Field of Classification Search
CPC . A61M 15/06; A61M 2205/13; F16K 31/002; F16K 31/025; F16K 99/0038; F16K 99/0044
See application file for complete search history.

(56) References Cited

U.S. PATENT DOCUMENTS

| | | | |
|---|---|---|---|
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,261,424 | A | 11/1993 | Sprinkel, Jr. |
| 5,388,574 | A | 2/1995 | Ingebrethsen et al. |
| 5,530,225 | A | 6/1996 | Hajaligol |
| 5,687,746 | A | 11/1997 | Rose et al. |
| 5,726,421 | A | 3/1998 | Fleischhauer et al. |
| 5,865,185 | A | 2/1999 | Collins et al. |
| 5,894,841 | A | 4/1999 | Voges |
| 6,125,853 | A | 10/2000 | Susa et al. |
| 6,155,268 | A | 12/2000 | Takeuchi |
| 7,117,867 | B2 | 10/2006 | Cox et al. |
| 7,832,410 | B2 | 11/2010 | Hon |
| 8,314,591 | B2 | 11/2012 | Terry et al. |
| 8,365,742 | B2 | 2/2013 | Hon |
| 8,499,766 | B1 | 8/2013 | Newton |
| 10,080,388 | B2 | 9/2018 | Sebastian et al. |
| 2005/0016550 | A1 | 1/2005 | Katase |
| 2006/0196518 | A1 | 9/2006 | Hon |
| 2008/0092912 | A1 | 4/2008 | Robinson et al. |
| 2009/0095311 | A1 | 4/2009 | Hon |
| 2009/0126745 | A1 | 5/2009 | Hon |
| 2009/0188490 | A1 | 7/2009 | Hon |
| 2009/0272379 | A1 | 11/2009 | Thorens et al. |
| 2011/0094523 | A1 | 4/2011 | Thorens et al. |
| 2011/0126848 | A1 | 6/2011 | Zuber et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2011/0290248 | A1 | 12/2011 | Schennum |
| 2012/0111347 | A1 | 5/2012 | Hon |
| 2012/0260927 | A1 | 10/2012 | Liu |
| 2012/0279512 | A1 | 11/2012 | Hon |
| 2013/0037041 | A1 | 2/2013 | Worm et al. |
| 2013/0056013 | A1 | 3/2013 | Terry et al. |
| 2013/0306084 | A1 | 11/2013 | Flick |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0209105 | A1 | 7/2014 | Sears et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2015/0028235 | A1 * | 1/2015 | Ichiki .................. F16K 99/0049 251/11 |
| 2018/0070632 | A1 | 3/2018 | Sur et al. |
| 2018/0199627 | A1 | 7/2018 | Bowen et al. |
| 2018/0206552 | A1 | 7/2018 | Sebastian et al. |
| 2019/0093783 | A1 | 3/2019 | Macko |
| 2020/0237002 | A1 * | 7/2020 | Bostock ................ F16K 31/025 |

FOREIGN PATENT DOCUMENTS

| | | | |
|---|---|---|---|
| CN | 201379072 | Y | 1/2010 |
| EP | 0 295 122 | A2 | 12/1988 |
| EP | 0 845 220 | A1 | 6/1998 |
| EP | 1 618 803 | A1 | 1/2006 |
| EP | 2216062 | A1 | 11/2010 |
| EP | 3387929 | A1 | 10/2018 |
| GB | 2469850 | A | 11/2010 |
| WO | 2003/034847 | A1 | 5/2003 |
| WO | 2004/080216 | A1 | 9/2004 |
| WO | 2005/099494 | A1 | 10/2005 |
| WO | 2007/131449 | A1 | 11/2007 |
| WO | 2018/138637 | A1 | 8/2018 |
| WO | 2019/115113 | A1 | 6/2019 |

* cited by examiner

SHAPE MEMORY MATERIAL FOR CONTROLLED LIQUID DELIVERY IN AN AEROSOL DELIVERY DEVICE

TECHNOLOGICAL FIELD

The present disclosure relates to aerosol delivery devices, and more particularly to an aerosol delivery device that includes a reservoir and a vaporizing assembly, which may utilize electrical power to aerosolize an aerosol precursor composition for the production of an aerosol. The aerosol precursor composition, which may incorporate materials and/or components that may be made or derived from tobacco or otherwise incorporate tobacco, is aerosolized by vaporizing assembly to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference in their entireties. See also, for example, the various types of smoking articles, aerosol delivery devices, and electrically powered heat generating sources referenced by brand name and commercial source in U.S. Pat. App. Pub. No. 2015/0216232, which is incorporated herein by reference in its entirety.

However, it would be desirable to provide an aerosol delivery device with enhanced functionality. In this regard, it is desirable to provide an aerosol delivery device and a cartridge for an aerosol delivery device with advantageous features.

BRIEF SUMMARY

The present disclosure relates to aerosol delivery devices, methods of forming such devices, and elements of such devices. The present disclosure particularly relates to aerosol delivery devices and cartridges for use with aerosol delivery devices.

In various implementations, the present disclosure provides a cartridge for use in an aerosol delivery device. In one implementation, the cartridge may comprise a housing defining a liquid reservoir configured to contain an aerosol precursor composition, an atomizer configured to receive the aerosol precursor composition and to produce an aerosol, the atomizer comprising a first liquid transport element, a second liquid transport element in fluid communication with the first liquid transport element, and a microvalve located between the liquid reservoir and the second liquid transport element. The microvalve may comprise a base member including at least one channel defined therethrough, and at least one actuating member at least a portion of which is constructed of a shape-memory material, and which is configured, in response to a stimulus, to move between a first position and a second position, wherein in the first position, the actuating member substantially blocks fluid flow from the liquid reservoir through the channel, and in the second position, the actuating member allows fluid flow from the liquid reservoir through the channel and to the second liquid transport element.

In some implementations, the atomizer may comprise a heating member, wherein at least a portion of the heating member is disposed proximate the first liquid transport element, and wherein the stimulus comprises heat generated by the heating member. In some implementations, the actuating member may comprise an extending cup positioned proximate the channel. In some implementations, the actuating member may comprise a lifting plate positioned proximate the channel. In some implementations, the base member may include a pair of channels, and wherein in the first position, the actuating member substantially blocks fluid flow from the liquid reservoir through the pair of channels, and in the second position, the actuating member allows fluid flow from the liquid reservoir through the pair of channels and to the second liquid transport element. Some implementations may further comprise a heat transfer component configured to transfer heat from the heating member to the actuating member. In some implementations, one end of the heat transfer component may be configured to contact the actuating member. In some implementations, at least a portion of the actuating member may be constructed of a shape-memory alloy material. In some implementations, at least a portion of the actuating member may be constructed of a shape-memory polymer material. In some implementations, the base member of the microvalve may be constructed of a substantially non-porous material. In some implementations, the base member of the microvalve may be constructed of a material that is at least partially porous.

In another implementation, the cartridge may comprise a housing defining a liquid reservoir configured to contain an aerosol precursor composition, an atomizer configured to receive the aerosol precursor composition and to produce an aerosol, the atomizer comprising a liquid transport element, and a microvalve located between the liquid reservoir and the liquid transport element. The microvalve may comprises a base member including at least one channel defined therethrough, and at least one actuating member comprising a spring and plunger mechanism, wherein at least a portion of the actuating member comprises a shape-memory material, which is configured, in response to a stimulus, to move between a first position and a second position, wherein in the first position, the actuating member substantially blocks fluid flow from the liquid reservoir through the channel, and in the second position, the actuating member allows fluid flow from the liquid reservoir through the channel and to the liquid transport element.

In some implementations, the atomizer may comprise a heating member, wherein at least a portion of the heating member is disposed proximate the liquid transport element, and wherein the stimulus comprises heat generated by the heating member. In some implementations, the base member may include a pair of channels, and wherein in the first position, the actuating member substantially blocks fluid flow from the liquid reservoir through the pair of channels, and in the second position, the actuating member allows fluid flow from the liquid reservoir through the pair of channels and to the liquid transport element. Some implementations may further comprise a heat transfer component configured to transfer heat from the heating member to the actuating member. In some implementations, one end of the heat transfer component may be configured to contact the actuating member. In some implementations, at least a portion of the actuating member may comprise a shape-memory alloy material. In some implementation, at least a portion of the actuating member may comprise a shape-memory polymer material. In some implementation, the base member of the microvalve may comprise a substantially non-porous material. In some implementations, the base member of the microvalve may comprise a material that is at least partially porous.

In various implementations, the present disclosure also provides an aerosol delivery device. In one implementation, the aerosol delivery device may comprise a control unit that includes a power source and a control component, and a cartridge comprising a housing defining a liquid reservoir configured to contain an aerosol precursor composition, an atomizer configured to receive the aerosol precursor composition and to produce an aerosol, the atomizer comprising a first liquid transport element, a second liquid transport element in fluid communication with the first liquid transport element, and a microvalve located between the liquid reservoir and the second liquid transport element. The control unit may be configured to generate the stimulus, wherein the microvalve comprises a base member including at least one channel defined therethrough, and at least one actuating member, at least a portion of which comprises a shape-memory material, and which is configured, in response to the stimulus, to move between a first position and a second position, wherein in the first position, the actuating member substantially blocks fluid flow from the liquid reservoir through the channel, and in the second position, the actuating member allows fluid flow from the liquid reservoir through the channel and to the second liquid transport element.

In some implementations, the atomizer may comprise a heating member, wherein at least a portion of the heating member is disposed proximate the liquid transport element, and wherein the stimulus comprises heat generated by the heating member. In some implementations, the actuating member may comprise an extending cup positioned proximate the channel. In some implementations, the actuating member may comprise a lifting plate positioned proximate the channel. In some implementations, the base member may include a pair of channels, and wherein in the first position, the actuating member substantially blocks fluid flow from the liquid reservoir through the pair of channels, and in the second position, the actuating member allows fluid flow from the liquid reservoir through the pair of channels. In some implementations, the cartridge may further comprise a heat transfer component configured to transfer heat from the heating member to the actuating member. In some implementations, one end of the heat transfer component may be configured to contact the actuating member. In some implementations, at least a portion of the actuating member may comprise a shape-memory alloy material. In some implementations, at least a portion of the actuating member may comprise a shape-memory polymer material. In some implementations, the base member may comprise a substantially non-porous material. In some implementations, the base member may comprise a material that is at least partially porous.

In another implementation the aerosol delivery device may comprise a control unit that includes a power source and a control component, and a cartridge comprising a housing defining a liquid reservoir configured to contain an aerosol precursor composition, an atomizer configured to receive the aerosol precursor composition and to produce an aerosol, the atomizer comprising a liquid transport element, and a microvalve located between the liquid reservoir and the liquid transport element. The microvalve may comprise a base member including at least one channel defined therethrough, and an actuating member at least a portion of which comprises a shape-memory material and which is configured, in response to a stimulus, to move between a first position and a second position, wherein in the first position, the actuating member substantially blocks fluid flow from the liquid reservoir through the channel, and in the second position, the actuating member allows fluid flow from the liquid reservoir through the channel and to the liquid transport element, and wherein the actuating member comprises a spring and plunger mechanism.

In some implementations, the atomizer may comprise a heating member, wherein at least a portion of the heating member is disposed proximate the liquid transport element, and wherein the stimulus comprises heat generated by the heating member. In some implementations, the base member may include a pair of channels, and wherein in the first position, the actuating member substantially blocks fluid flow from the liquid reservoir through the pair of channels, and in the second position, the actuating member allows fluid flow from the liquid reservoir through the pair of channels. Some implementations may further comprise a heat transfer component configured to transfer heat from the heating member to the actuating member. In some implementations, one end of the heat transfer component may be configured to contact the actuating member. In some implementations, at least a portion of the actuating member may comprise a shape-memory alloy material. In some implementations, at least a portion of the actuating member may comprise a shape-memory polymer material. In some implementations, the base member may comprise a substantially non-porous material. In some implementations, the base member may comprise a material that is at least partially porous.

These and other features, aspects, and advantages of the disclosure will be apparent from a reading of the following detailed description together with the accompanying drawings, which are briefly described below.

BRIEF DESCRIPTION OF THE DRAWINGS

In order to assist the understanding of aspects of the disclosure, reference will now be made to the appended drawings, which are not necessarily drawn to scale and in which like reference numerals refer to like elements. The drawings are examples only, and should not be construed as limiting the disclosure.

DETAILED DESCRIPTION

Figure 1:
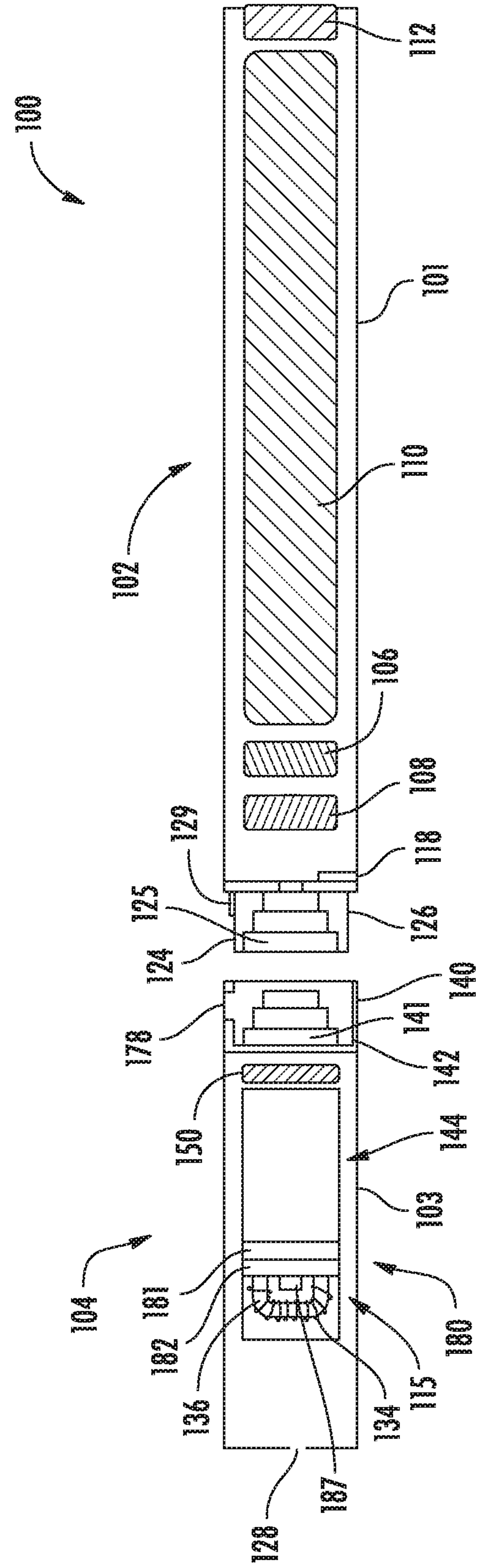
FIG. 1 illustrates a side cross-section schematic view of an aerosol delivery device comprising a cartridge and a control unit, according to an example implementation of the present disclosure.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to aerosolize a material (preferably without combusting the material to any significant degree and/or without significant chemical alteration of the material) to form an inhalable substance, and components of such devices have the form of articles that most preferably are sufficiently compact to be considered hand-held devices. That is, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In some embodiments, components of aerosol delivery devices may be characterized as electronic cigarettes, and those electronic cigarettes most preferably incorporate tobacco and/or components derived from tobacco, and hence deliver tobacco derived components in aerosol form.

Aerosol generating devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also may be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure may comprise some combination of a power source (i.e., an electrical power source), at least one control component (e.g., means for actuating, controlling, regulating and ceasing power, such as by controlling electrical current flow from the power source to other components of the article—e.g., a microcontroller or microprocessor), an atomizer, which is some implementations may comprise heater or heat generation member (e.g., an electrical resistance heating element or other component, which alone or in combination with one or more further elements may be commonly referred to as an "atomizer"), a liquid composition (e.g., commonly an aerosol precursor composition liquid capable of yielding an aerosol upon application of sufficient heat, such as ingredients commonly referred to as "smoke juice,"

"e-liquid" and "e-juice"), and a mouthpiece or mouth region for allowing draw upon the aerosol delivery device for aerosol inhalation (e.g., a defined airflow path through the article such that aerosol generated may be withdrawn therefrom upon draw).

Alignment of the components within the aerosol delivery device may be variable. In specific embodiments, the aerosol precursor composition may be located between two opposing ends of the device (e.g., within a reservoir of a cartridge, which in certain circumstances is replaceable and disposable or refillable). Other configurations, however, are not excluded. Generally, the components are configured relative to one another so that energy from the atomizer volatilizes the aerosol precursor composition (as well as one or more flavorants, medicaments, or the like that may likewise be provided for delivery to a user) and forms an aerosol for delivery to the user. When the atomizer energizes (e.g., by heating) the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

More specific formats, configurations and arrangements of components within the aerosol delivery devices of the present disclosure will be evident in light of the further disclosure provided hereinafter. Additionally, the selection and arrangement of various aerosol delivery device components may be appreciated upon consideration of the commercially available electronic aerosol delivery devices, such as those representative products referenced in the background art section of the present disclosure.

FIG. 1 illustrates an aerosol delivery device comprising a cartridge and a control unit, according to an example implementation of the present disclosure. In particular, FIG. 1 illustrates a side cross-section schematic view of an aerosol delivery device 100. As depicted in the figure, the aerosol delivery device 100 of the depicted implementation includes a control unit 102 and a cartridge 104, which may be permanently or detachably aligned in a functioning relationship with the control unit 102. In some implementations a connection between a cartridge and a control unit may be substantially permanent, whereas in other implementations (such as the depicted implementation), a connection therebetween may be releasable such that, for example, the control unit may be reused with one or more additional cartridges that may be disposable and/or refillable. In various implementations, a variety of different means of engagement may be used to couple a cartridge and a control unit together. For example, in some implementations the cartridge and the control unit may be coupled via one or more of a snap fit engagement, a press fit engagement, a threaded engagement, and a magnetic engagement. It should be noted that the components depicted in this and the other figures are representative of the components that may be present in a control unit and/or cartridge and are not intended to limit the scope of the control unit and/or cartridge components that are encompassed by the present disclosure.

In various implementations, the aerosol delivery device 100 may have a variety of different shapes. For example, in some implementations (such as the depicted implementation) the aerosol delivery device 100 may be substantially rod-like or substantially tubular shaped or substantially cylindrically shaped. In other implementations, other shapes and dimensions are possible (e.g., rectangular, oval, hexagonal, prismatic, and multifaceted shapes, or the like). In still other implementations, the cartridge and the control unit may have different shapes.

In the depicted implementation, the control unit 102 and the cartridge 104 include components adapted to facilitate mechanical engagement therebetween. Although a variety of other configurations are possible, the control unit 102 of the depicted implementation includes a coupler 124 that defines a cavity 125 therein. Likewise, the cartridge 104 includes a base 140 adapted to engage the coupler 124 of the control unit 102. A coupler and a base that may be useful according to the present disclosure are described in U.S. Pat. Pub. No. 2014/0261495 to Novak et al., the disclosure of which is incorporated herein by reference in its entirety.

In the depicted implementation, the base 140 of the cartridge 104 includes a projection 141 adapted to fit within the cavity 125 such that stable mechanical and electrical connections between the control unit 102 and the cartridge 104 are established. In particular, the coupler 124 of the depicted implementation may define an outer periphery 126 configured to mate with an inner periphery 142 of the base 140. In one implementation the inner periphery 142 of the base 140 may define a diameter that is substantially equal to, or slightly greater than, a diameter of the outer periphery 126 of the coupler 124. Further, the coupler 124 may define one or more protrusions 129 at the outer periphery 126 configured to engage one or more recesses 178 defined at the inner periphery 142 of the base 140. It should be noted, however, that in other implementations various other structures, shapes, and/or components may be employed to couple the control unit and the cartridge.

In specific implementations, one or both of the control unit 102 and the cartridge 104 may be referred to as being disposable or as being reusable. For example, in some implementations the control unit may have a replaceable battery or a rechargeable battery and thus may be combined with any type of recharging technology, including connection to a wall charger, connection to a car charger (e.g., cigarette lighter receptacle, USB port, etc.), connection to a computer, any of which may include a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power a heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

As illustrated in the figure, the control unit 102 may be formed of a control unit housing 101 that includes a control component 106 (e.g., a printed circuit board (PCB), an integrated circuit, a memory component, a microcontroller, or the like, as well as a resistance temperature detector for temperature control), a flow sensor 108, a battery 110, and a light-emitting diode (LED) 112, which components may be variably aligned. Some example types of electronic components, structures, and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference in their entireties. Some examples of batteries that may be applicable to the present disclosure are described in U.S. Pat. App. Pub. No. 2010/0028766 to Peckerar et al., the disclosure of which is incorporated herein by reference in its entirety. In some implementations, further indicators (e.g., a haptic feedback component, an audio feedback component, or the like) may be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference in their entireties. It should be understood that in various implementations not all of the illustrated elements may be required. For example, in some implementations an LED may be absent or may be replaced with a different indicator, such as a vibrating indicator. Likewise, a flow sensor may be replaced with a manual actuator, such as, for example, one or more manually actuated push buttons.

In the depicted implementation, the cartridge 104 may be formed of a cartridge housing 103, which may define a liquid reservoir 144 configured to contain a liquid composition. In some implementations, the liquid reservoir may be part of the cartridge housing (such as, for example, comprising a molded feature of the cartridge housing), while in other implementations, the liquid reservoir may comprise a separate part. In various implementations, the liquid composition contained in the liquid reservoir 144 may comprise an aerosol precursor composition. Some examples of types of substrates, reservoirs, or other components for supporting a liquid composition are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety.

In some implementations, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. Pub. No. 2015/0335070 to Sears et al., the disclosure of which is incorporated herein by reference in its entirety. In another regard, the tobacco may be provided in the form of an extract, such as a spray dried extract that incorporates many of the water-soluble components of tobacco. Some implementations may include supercritical carbon dioxide tobacco extracts. In some implementations, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine). In other implementations, non-tobacco materials alone may form the aerosol precursor composition.

In the depicted implementation, the liquid composition, sometimes referred to as an aerosol precursor composition or a vapor precursor composition or "e-liquid", may comprise a variety of components, which may include, by way of example, a polyhydric alcohol (e.g., glycerin, propylene glycol, other glycols, or a mixture thereof), nicotine, tobacco, tobacco extract, organic acids, inorganic acids, water, and/or flavorants. Representative types of aerosol precursor components and formulations are also set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

The amount of aerosol precursor that is incorporated within the aerosol delivery system is such that the aerosol generating device provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, up to about 1 ml or more, about 2 ml or more, about 5 ml or more, or about 10 ml or more of the aerosol precursor composition may be included.

In various implementations, the liquid composition may include a flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components is variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Referring back to FIG. 1, the liquid reservoir 144 of the depicted implementation may be in fluid communication with (either directly or, such as in the depicted implementation, through one or more additional components) at least a portion of an atomizer 115. In some implementations, the liquid reservoir 144 may comprise a container (e.g., formed of walls substantially impermeable to the liquid composition). In other implementations, the liquid reservoir may comprise a fibrous reservoir. In some implementations, the walls of the liquid reservoir may be flexible and/or collapsible, while in other implementations the walls of the liquid reservoir may be substantially rigid. In some implementations, the liquid reservoir may be substantially sealed to prevent passage of the liquid composition therefrom except via any specific openings or conduits provided expressly for passage of the liquid composition, such as through one or more transport elements as otherwise described herein. In some implementations, the liquid reservoir may comprise one or more layers of nonwoven fibers substantially formed into the shape of a tube encircling an interior of the cartridge housing, wherein the fibers may comprise polycarbonate, silicone, polyester, polyethylene, polypropylene, ceramic, fiberglass, or cellulose acetate.

In the depicted implementation, the atomizer 115 includes a first liquid transport element 136 adapted to wick or otherwise transport the aerosol precursor composition stored in the liquid reservoir 144 to a heating member 134, which is disposed proximate the first liquid transport element 136. For example, in the depicted implementation at least a portion of the heating member 134 comprises a wire coil that is configured to be wrapped around at least a portion of the first liquid transport element 136. Although a variety of other configurations are possible, the first liquid transport element 136 of the depicted implementation generally has a U-shape comprising a central portion and two leg portions that extend from opposite ends of the central portion. In the depicted implementation, at least a portion of the heating member 134 is configured to be wrapped around at least a portion of the first liquid transport element 136 (e.g., at least a portion of the central portion of the first liquid transport element, or at least a portion of the central and leg portions of the first liquid transport element). As such, when the heating member 134 is activated, at least a portion of the liquid composition in the first liquid transport element 136 may be vaporized.

In the depicted implementation, the control unit housing 101 includes an air intake 118, which may comprise an opening in the housing proximate the coupler 124 allowing for passage of ambient air into the control unit housing 101 where it then passes through the cavity 125 of the coupler 124, the projection 141 of the cartridge 104, and eventually into or around the atomizer 115, where it may be mixed with the vaporized aerosol precursor composition to comprise the aerosol that is delivered to the user. It should be noted that in other implementations the air intake 118 is not limited being on or adjacent the control unit housing 101. For example, in some implementations, an air intake may be formed through the cartridge housing 103 (e.g., such that it does not enter the control unit 102) or some other portion of the aerosol delivery device 100. In the depicted implementation, an opening 128 may be present in the cartridge housing 103 (e.g., at a mouthend of the cartridge 104) to allow for egress of the formed aerosol from the cartridge 104, such as for delivery to a user drawing on the mouthend of the cartridge 104.

In various implementations, the first liquid transport element 136 may be formed of one or more materials configured for transport of a liquid, such as by capillary action. For example, in some implementations the first liquid transport element 136 may be formed of, for example, fibrous materials (e.g., organic cotton, cellulose acetate, regenerated cellulose fabrics, glass fibers), porous ceramics (alumina, silica, zirconia, SiC, SiN, AlN, etc.), porous metals, porous carbon, graphite, porous glass, sintered glass beads, sintered ceramic beads, capillary tubes, porous polymers, or the like. The liquid transport element thus may be any material that contains an open pore network (i.e., a plurality of pores that are interconnected so that fluid may flow from one pore to another in a plurality of direction through the element). The pores can be nanopores, micropores, macropores or combinations thereof. As further discussed herein, some implementations of the present disclosure may particularly relate to the use of non-fibrous transport elements. As such, in some embodiments, fibrous transport elements may be expressly excluded. Alternatively, combinations of fibrous transport elements and non-fibrous transport elements may be utilized. In some embodiments, the first liquid transport element may be a substantially solid non-porous material, such as a polymer or dense ceramic or metals, configured to channel liquid through apertures or slots while not necessarily relying upon wicking through capillary action. Such a solid body may be used in combination with a porous absorptive pad. The absorptive pad may be formed of silica-based fibers, organic cotton, rayon fibers, cellulose acetate, regenerated cellulose fabrics, highly porous ceramic or metal mesh, etc.

As noted, in some implementations the first liquid transport element may be formed partially or completely from a porous monolith, such as a porous ceramic, a porous glass, porous polymer, or the like. Some example monolithic materials that may be suitable for use according to implementations of the present disclosure are described, for example, in U.S. Pat. App. Pub. No. 2017/0188626 to Davis et al., and U.S. Pat. App. Pub. No. 2014/0123989 to LaMothe, the disclosures of which are incorporated herein by reference in their entireties. In some implementations, the porous monolith may form a substantially rigid wick. In particular, the transport element may be substantially a single, monolithic material rather than a bundle of individual fibers as known in the art.

Various implementations of materials configured to produce heat when electrical current is applied therethrough may be employed to form the heating member 134. Example materials from which the wire coil may be formed include Kanthal (FeCrAl), nichrome, nickel, stainless steel, indium tin oxide, tungsten, molybdenum disilicide ($MoSi_2$), molybdenum silicide (MoSi), molybdenum disilicide doped with aluminum ($Mo(Si,Al)_2$), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics). In some implementations, the heating member 134 may be resistive heating element. In other implementations, the heating member may be configured to generate heat through induction. In some implementations, the heating member 134 may be coated by heat conductive ceramics such as aluminum nitride, silicon carbide, beryllium oxide, alumina, silicon nitride, or their composites.

The cartridge 104 may also include at least one electronic component 150, which may include an integrated circuit, a memory component, a sensor, or the like, although such a component need not be included. In those implementations that include such a component, the electronic component 150 may be adapted to communicate with the control component 106 and/or with an external device by wired or wireless means. In various implementations, the electronic component 150 may be positioned anywhere within the cartridge 104 or its base 140. Although in the depicted implementation the control component 106 and the flow sensor 108 are illustrated separately, it should be noted that in some implementations the control component and the flow sensor may be combined as an electronic circuit board with the air flow sensor attached directly thereto. Additionally, in some implementations the control component 106 may be considered as inclusive of a resistance temperature detector. In other implementations, a resistance temperature detector may be incorporated with the electronic component 150. In some embodiments, the air flow sensor may comprise its own circuit board or other base element to which it can be attached. In some embodiments, a flexible circuit board may be utilized. A flexible circuit board may be configured into a variety of shapes, include substantially tubular shapes. Configurations of a printed circuit board and a pressure sensor, for example, are described in U.S. Pat. Pub. No. 2015/0245658 to Worm et al., the disclosure of which is incorporated herein by reference. Additional types of sensing or detection mechanisms, structures, and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, when a user draws on the article 100, airflow may be detected by the flow sensor 108, and the heating member 134 may be activated, which may vaporize the liquid composition. As noted above, drawing upon the mouthend of the article 100 causes ambient air to enter the air intake 118 and pass through the cavity 125 in the coupler 124 and the central opening in the projection 141 of the base 140. In the cartridge 104, the drawn air combines with the formed vapor to form the aerosol. The aerosol is whisked, aspirated, or otherwise drawn away from the heating element 134 and out of the opening 128 in the mouthend of the article 100. As noted, in other implementations, in the absence of an airflow sensor, the heating element 134 may be activated manually, such as by a push button. Additionally, in some implementations, the air intake may occur through the cartridge or between the cartridge and the control unit.

In some implementations, one or more input elements may be included with the aerosol delivery device (and may replace or supplement an airflow sensor, pressure sensor, or manual push button). In various implementations, an input element may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference in its entirety. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

In some embodiments, an input element may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference in its entirety. In such implementations, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Yet other features, controls or components that may be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

As will be discussed in more detail below, the cartridge 104 of the depicted implementation also includes a microvalve 180 and a second liquid transport element 182 that is in fluid communication with the first liquid transport element. In various implementations, the microvalve is configured to move between a first position and a second position (and vice versa) based on heat (or lack of heat) produced by the heating member 134. In various implementations, the first and second positions represent open and closed positions (or vice versa), wherein in the open position, fluid is permitted to flow from the liquid reservoir 144 through the microvalve, and in the closed position, the microvalve substantially blocks fluid flow from the liquid reservoir 144. It should be noted in other implementations, the microvalve may be configured to move to and from one or more intermediate positions, such as one or more positions between the first and second positions. In such a manner, a microvalve of the present disclosure may provide flow control in addition to (or as an alternative to) providing a two-way valve function.

Figure 2:
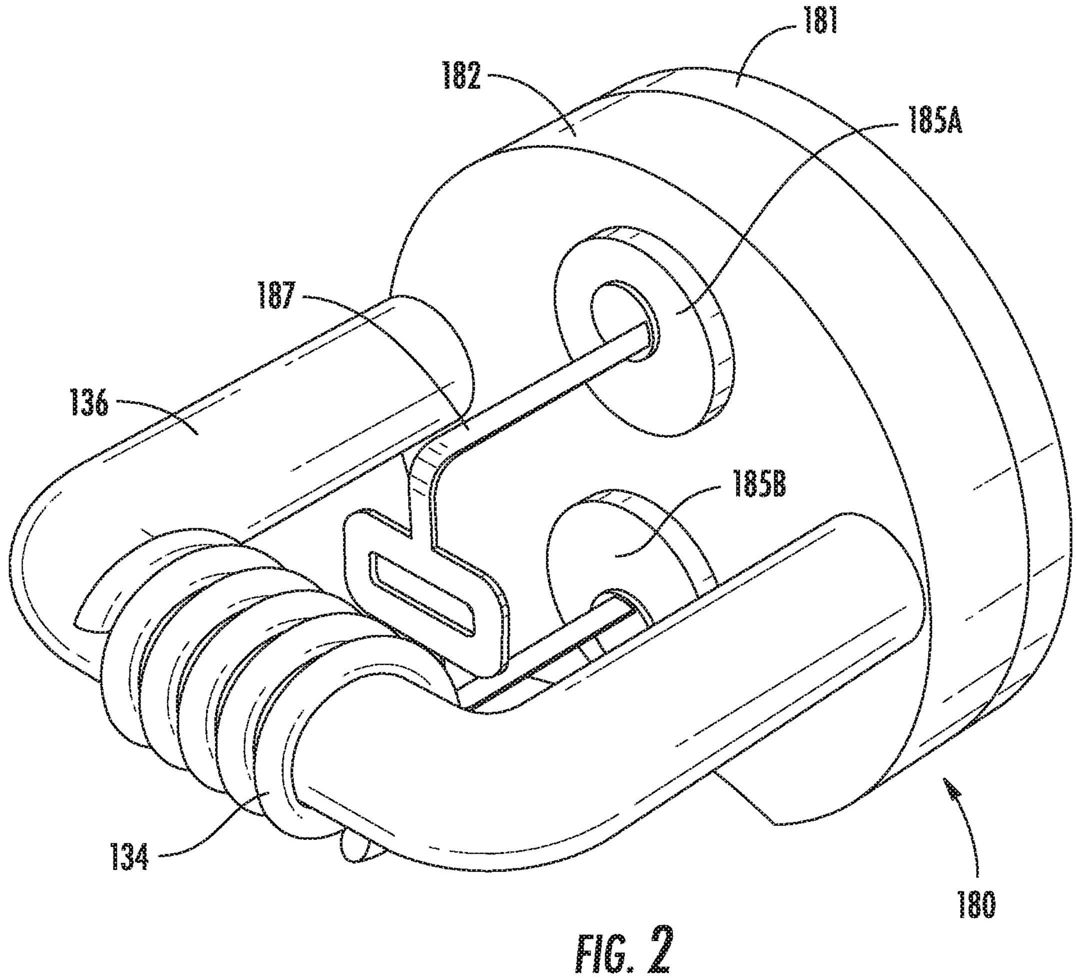
FIG. 2 illustrates a perspective view of a portion of a cartridge wherein the microvalve is shown in an open position, according to an example implementation of the present disclosure.

FIG. 2 illustrates a perspective view of a portion of a cartridge wherein the microvalve 180 is shown in an open position, according to an example implementation of the present disclosure. In particular, FIG. 2 illustrates a portion of the heating member 134, first liquid transport element 136, second liquid transport element 182, and microvalve 180 of FIG. 1. In the depicted implementation, the microvalve 180 comprises a base member 181 that includes a pair of channels (not visible in this figure) and a pair of actuating members 185A, 185B, which, as will be described in more detail below, are configured to move between open and closed positions (and vice versa). The depicted implementation also includes a heat transfer component 187 that is configured to transfer heat from the heating member 134 to the actuating members 185A, 185B wherein in the first position, the actuating members substantially block fluid flow from the liquid reservoir through the channel, and in the second position, the actuating members allow fluid flow from the liquid reservoir through the channel and to the second liquid transport element.

In the depicted implementation, the second liquid transport element 182 is in fluid communication with the first liquid transport element 136. Although in various implementations fluid communication may be established between the second liquid transport element 182 and the first liquid transport element 136 in a variety of different ways, in the depicted implementation the ends of the leg portions of the first liquid transport element 136 contact a top surface of the second liquid transport element 182. In other implementations, for example, the ends of the legs may be embedded into the second liquid transport element, such as for example in recesses in the surface of the second liquid transport element. In various implementations, the second liquid transport element may comprise one or more materials configured for transport of a liquid, such as by capillary action. For example, in some implementations the second liquid transport element can be formed of, for example, fibrous materials (e.g., organic cotton, cellulose acetate, regenerated cellulose fabrics, glass fibers), porous ceramics (alumina, silica, zirconia, SiC, SiN, AlN, etc.), porous metals, porous carbon, graphite, porous glass, sintered glass beads, sintered ceramic beads, capillary tubes, porous polymers, or the like. The second liquid transport element thus can be any material that contains an open pore network (i.e., a plurality of pores that are interconnected so that fluid may flow from one pore to another in a plurality of direction through the element). The pores can be nanopores, micropores, macropores or combinations thereof. As further discussed herein, some embodiments of the present disclosure can particularly relate to the use of non-fibrous transport elements. As such, in some embodiments, fibrous transport elements can be expressly excluded. Alternatively, combinations of fibrous transport elements and non-fibrous transport elements may be utilized. In some implementations, the second liquid transport element may be a substantially solid non-porous material, such as a polymer or dense ceramic or metals, configured to channel liquid through apertures or slots while not necessarily relying upon wicking through capillary action. Such a solid body may be used in combination with a porous absorptive pad. The absorptive pad can be formed of silica-based fibers, organic cotton, rayon fibers, cellulose acetate, regenerated cellulose fabrics, highly porous ceramic or metal mesh, etc.

As noted, in some implementations the second liquid transport element 182 may be formed partially or completely from a porous monolith, such as a porous ceramic, a porous glass, porous polymer, or the like. Some example monolithic materials that may be suitable for use according to implementations of the present disclosure are described, for example, in U.S. Pat. App. Pub. No. 2017/0188626 to Davis et al., and U.S. Pat. App. Pub. No. 2014/0123989 to LaMothe, the disclosures of which are incorporated herein by reference in their entireties. In some implementations the porous monolith may form a substantially rigid wick. In particular, the transport element can be substantially a single, monolithic material rather than a bundle of individual fibers as known in the art.

Although other configurations are possible, in the depicted implementation the thickness of the second liquid transport element 182 is larger than the thickness of the base member 181. In the depicted implementation, the base member 181 may comprise a porous material, or a substantially non-porous material, such as, for example, substantially non-porous polymeric, ceramic, or metal materials. In other implementations, the base member may comprise a low porosity material. For those implementations in which the base member 181 comprises a porous material, when the actuating members are in the closed position, the base member 181 may provide wicking through the base member such as, for example, wicking with a low diffusion rate. Consequently, the liquid composition may be absorbed into the second liquid transport element 182 through the channels of the base member 181 (e.g., via a high wicking rate) and/or through the base member 181 itself (e.g., via a low wicking rate). In the case of a porous material for the base member, reference is made to the list of possible materials for the first or second liquid transport elements.

Figure 3:
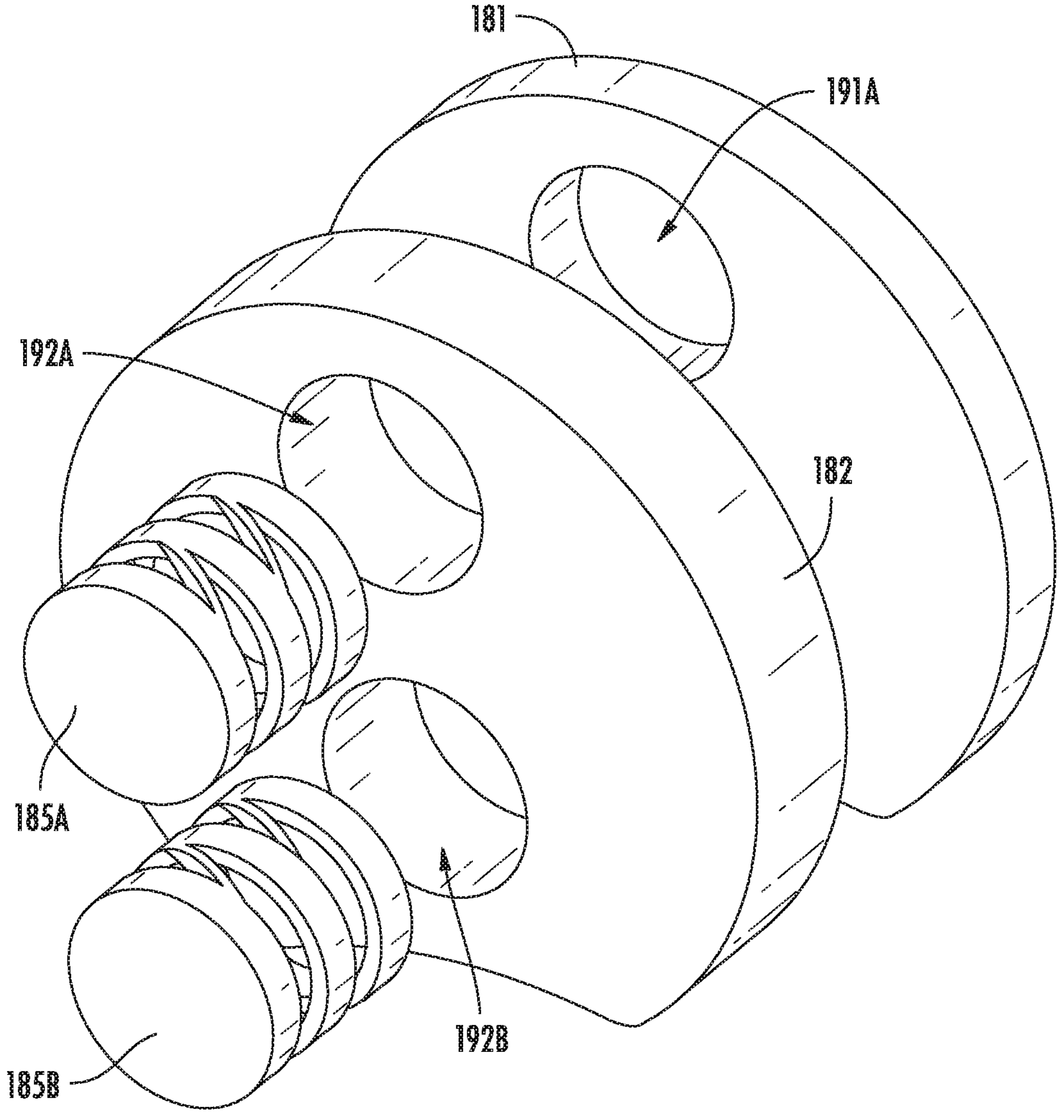
FIG. 3 illustrates an exploded perspective view of a portion of the cartridge of FIG. 2 wherein the microvalve is shown in an open position, according to an example implementation of the present disclosure.
Figure 4:
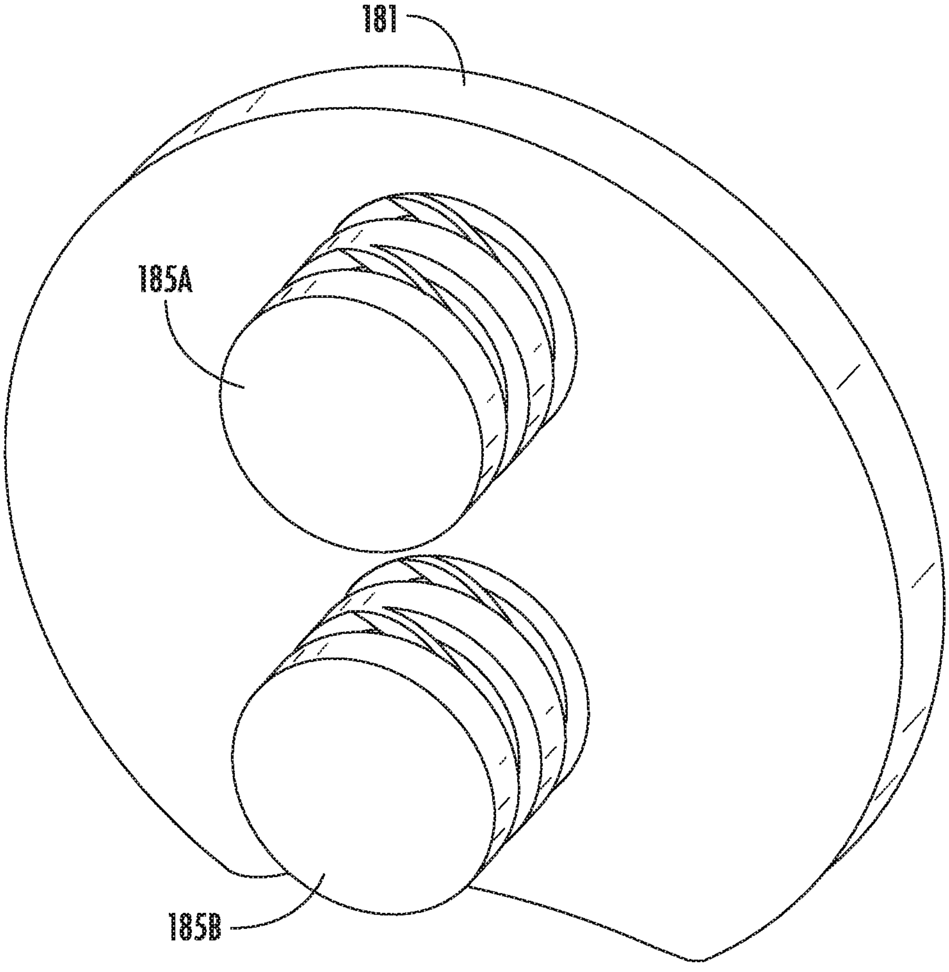
FIG. 4 illustrates a perspective view of a portion of the cartridge of FIG. 2 wherein the microvalve is shown in an open position, according to an example implementation of the present disclosure.
Figure 5A:
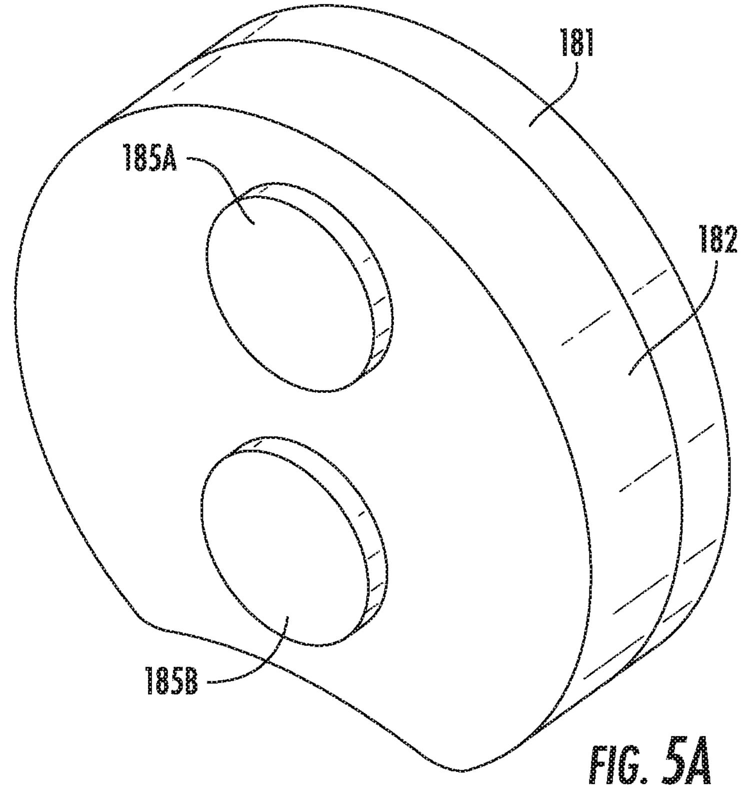
FIG. 5A illustrates a perspective view of a portion of the cartridge of FIG. 2 wherein the microvalve is shown in an open position, according to an example implementation of the present disclosure.
Figure 5B:
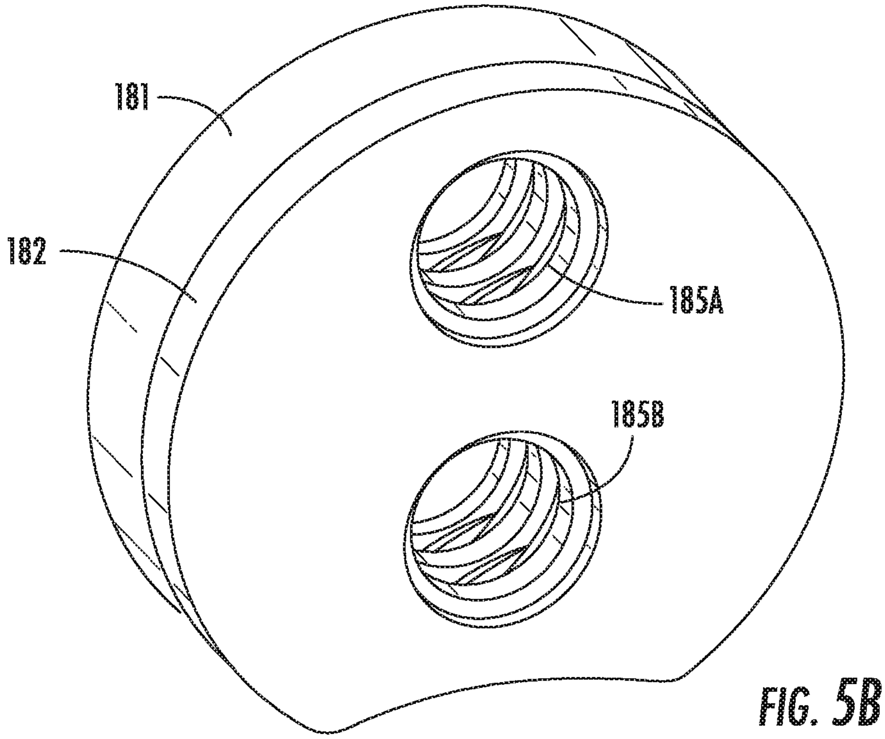
FIG. 5B illustrates a reverse perspective view of a portion of the cartridge of FIG. 2 wherein the microvalve is shown in an open position, according to an example implementation of the present disclosure.
Figure 6:
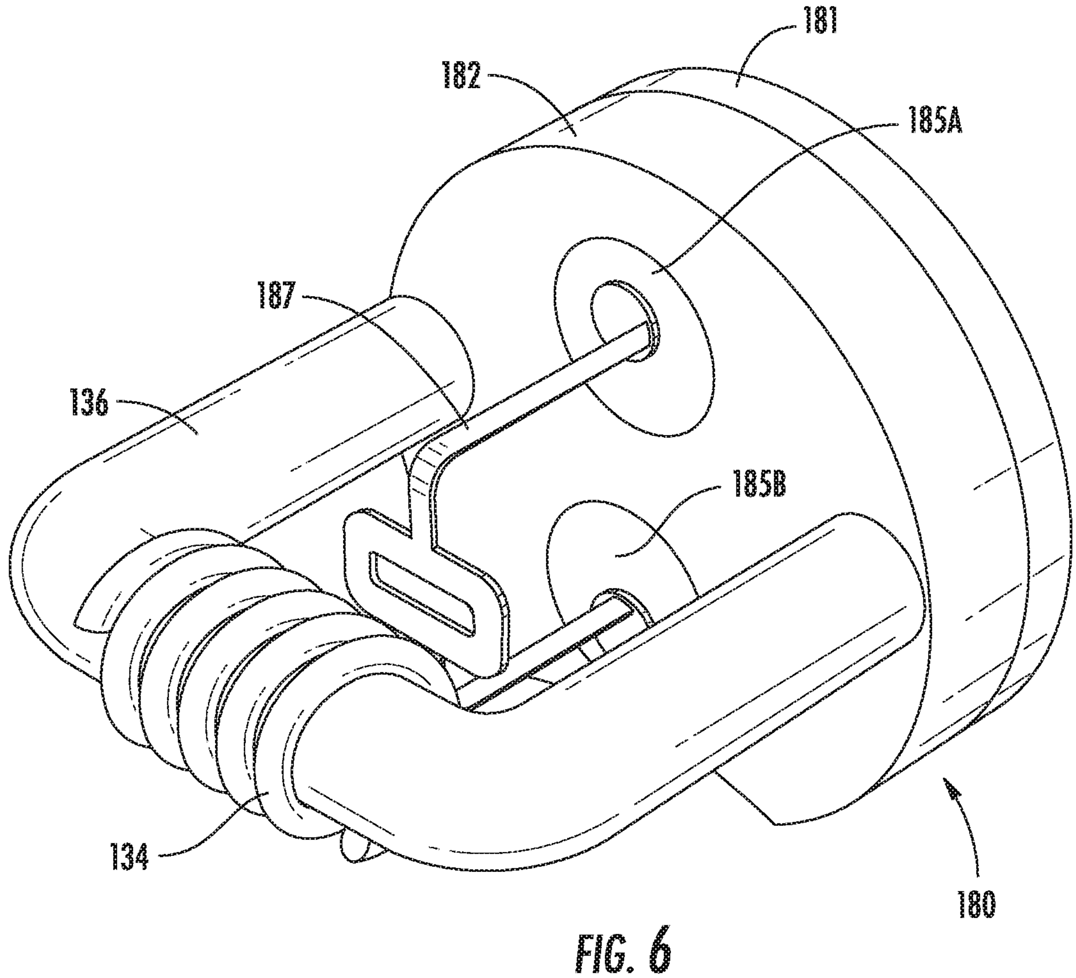
FIG. 6 illustrates a perspective view of a portion of the cartridge of FIG. 2 wherein the microvalve is shown in a closed position, according to an example implementation of the present disclosure.
Figure 7:
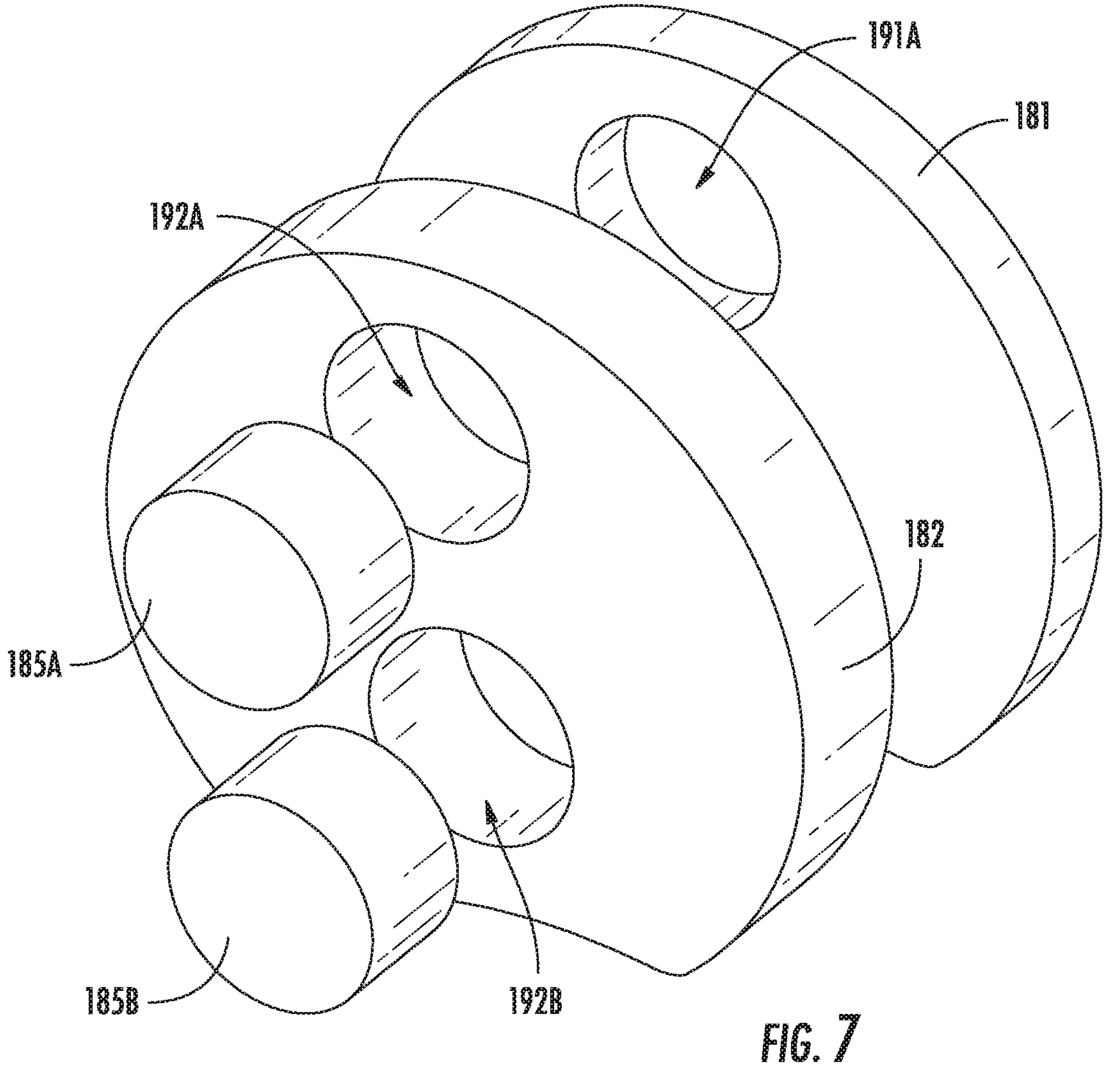
FIG. 7 illustrates an exploded perspective view of a portion of the cartridge of FIG. 2 wherein the microvalve is shown in a closed position, according to an example implementation of the present disclosure.
Figure 8:
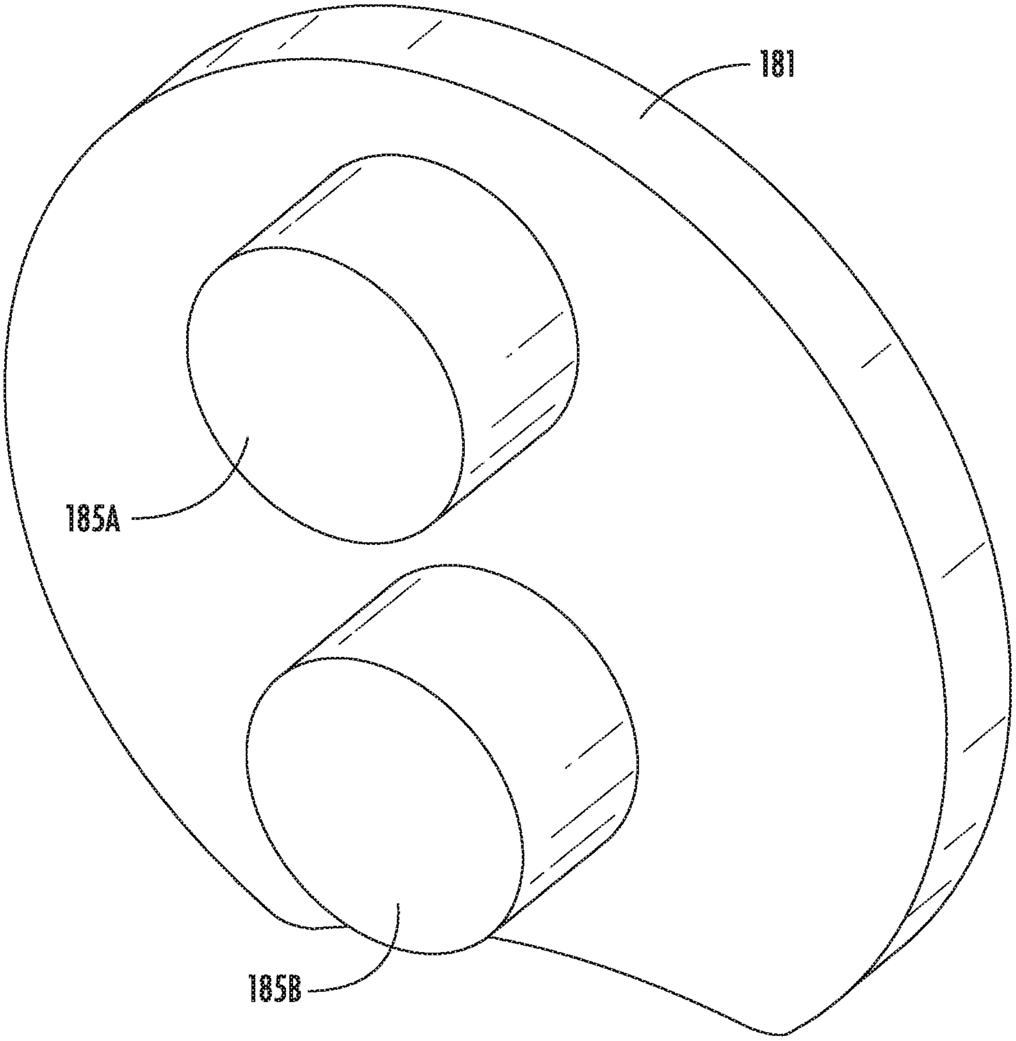
FIG. 8 illustrates a perspective view of a portion of the cartridge of FIG. 2 wherein the microvalve is shown in a closed position, according to an example implementation of the present disclosure.
Figure 9A:
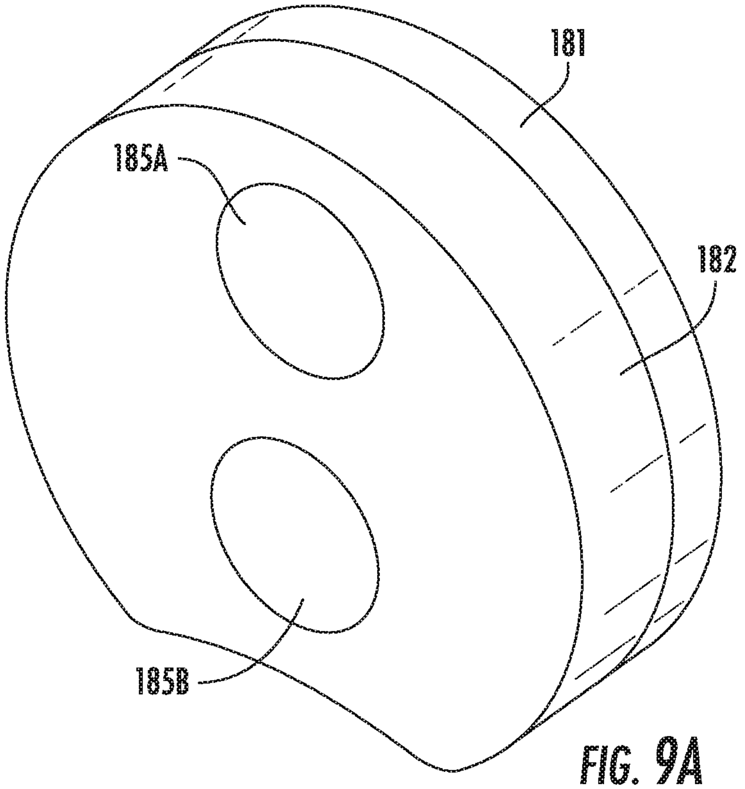
FIG. 9A illustrates a perspective view of a portion of the cartridge of FIG. 2 wherein the microvalve is shown in a closed position, according to an example implementation of the present disclosure.
Figure 9B:
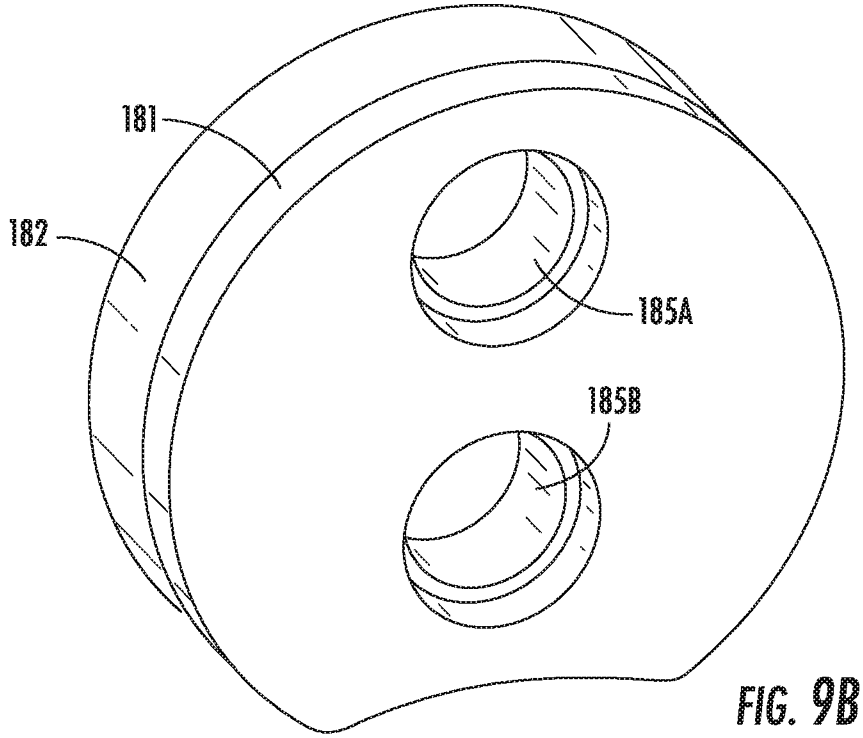
FIG. 9B illustrates a reverse perspective view of a portion of the cartridge of FIG. 2 wherein the microvalve is shown in a closed position, according to an example implementation of the present disclosure.

FIG. 3 illustrates an exploded perspective view of a portion of the cartridge of FIG. 2 wherein the microvalve is shown in the open position. In particular, FIG. 3 shows an exploded view of the base member 181, the second liquid transport element 182, and the pair of actuating members 185A, 185B of FIG. 1 in an open position. Likewise, FIG. 4 shows a perspective view of the base member 181 and actuating member 185A, 185B assembled together and in the open position, and FIGS. 5A and 5B show opposite perspective views of the base member 181, second liquid transport element 182, and actuating members 185A, 185B assembled together and in the open position. Conversely, FIG. 6 illustrates a portion of the heating member 134, first liquid transport element 136, second liquid transport element 182, and microvalve 180 of FIG. 1 wherein the microvalve is shown in the closed position. FIG. 7 illustrates an exploded perspective view of the base member 181, the second liquid transport element 182, and the pair of actuating members 185A, 185B in the closed position. Likewise, FIG. 8 shows a perspective view of the base member 181 and actuating member 185A, 185B assembled together and in the closed position, and FIGS. 9A and 9B show opposite perspective views of the base member 181, second liquid transport element 182, and actuating members 185A, 185B assembled together and in the closed position.

Referring to FIGS. 3-5B, in the depicted implementation the second liquid transport element 182 includes a pair of channels 192A, 192B defined by apertures that extend through the thickness of the second liquid transport element 182. Although in various implementations the channels may take any form, in the depicted implementation the channels 192A, 192B have substantially cylindrical shapes. Likewise, the base member 181 includes a pair of channels 191A, 191B defined by respective apertures over which the pair of actuating members 185A, 185B are assembled. Although in various implementations the channels may take any form, the channels 191A, 191B of the depicted implementation have substantially cylindrical shapes that substantially match (e.g., in location and diameter) the channels of the second liquid transport element 182. As such, when the depicted implementation is assembled, the channels 191A, 191B of the base member 181 are substantially aligned with the channels 192A, 192B of the second liquid transport element 182.

In the depicted implementation, the actuating members 185A, 185B are positioned proximate the channels 191A, 191B of the base member 181, respectively. More particularly, the actuating members 185A, 185B of the depicted implementation are configured to cover the channels 191A, 191B of the base member 181 and comprise extending cups that are made of a shape-memory material. In some implementations, the shape-memory material may be a shape-memory alloy. In other implementations, the shape-memory material may be a shape-memory polymer. Some descriptions of shape memory alloys can be found in U.S. Pat. No. 10,080,388 to Sebastian et al., and U.S. Pat. App. Pub. No. 2018/0174500 to Sebastian et al., which are incorporated herein by reference in their entireties.

Shape-memory alloys generally refer to a group of metallic materials that demonstrate the ability to return to some previously defined shape or size when subjected to an appropriate stimulus, which may vary across various implementations. For example, in some implementations the stimulus may comprise a change in temperature. In other implementations, the stimulus may comprise a change in an electric or magnetic field. In other implementations, the stimulus may comprise exposure to light. In other implementations, the stimulus may comprise a change in pH level. In still other implementations, the stimulus may comprise a chemical reaction. Some shape-memory alloys are configured to change phase and/or crystal structure resulting in a shape memory effect. For example, some shape-memory alloys are capable of undergoing phase transitions in which their yield strength, stiffness, dimension and/or shape are altered as a function of temperature. Generally, in the low temperature, or martensite phase, shape memory alloys can be elastically deformed and upon exposure to some higher temperature will transform to an austenite phase, or parent phase, returning to their shape prior to the deformation.

Shape-memory alloys exist in several different temperature-dependent phases. The most commonly utilized of these phases are the so-called martensite and austenite phases. In the following discussion, the martensite phase generally refers to the more deformable, lower temperature phase whereas the austenite phase generally refers to the more rigid, higher temperature phase. When the shape-memory alloy is in the martensite phase and is heated, it begins to change into the austenite phase. The temperature at which this phenomenon starts is often referred to as austenite start temperature ($A_s$). The temperature at which this phenomenon is complete is called the austenite finish temperature ($A_f$).

When the shape-memory alloy is in the austenite phase and is cooled, it begins to change into the martensite phase, and the temperature at which this phenomenon starts is referred to as the martensite start temperature ($M_s$). The temperature at which austenite finishes transforming to martensite is called the martensite finish temperature ($M_f$). Generally, the shape-memory alloys are softer and more easily deformable in their Martensitic phase and are harder, stiffer, and/or more rigid in the austenitic phase.

Some shape memory alloys may exhibit a one-way shape memory effect, an intrinsic two-way effect, or an extrinsic two-way shape memory effect depending on the alloy composition and processing history. Annealed shape memory alloys typically only exhibit the one-way shape memory effect. Sufficient heating subsequent to low-temperature deformation of the shape memory material will induce the martensite to austenite type transition, and the material will recover the original, annealed shape. Hence, one-way shape memory effects are observed upon heating. Active materials comprising shape memory alloy compositions that exhibit one-way memory effects do not automatically reform, and require an external mechanical force to return the shape to its previous configuration.

Intrinsic and extrinsic two-way shape memory alloys are characterized by a shape transition (i.e., from a first shape to a second shape) both upon heating from the martensite phase to the austenite phase, as well as an additional shape transition (i.e., from the second shape to the first shape) upon cooling from the austenite phase back to the martensite phase. Active materials that exhibit an intrinsic shape memory effect are fabricated from a shape memory alloy composition that will cause the active materials to automatically reform themselves as a result of the above noted phase transformations. Intrinsic two-way shape-memory behavior must be induced in the shape memory material through processing. Such procedures include extreme deformation of the material while in the martensite phase, heating-cooling under constraint or load, or surface modification such as laser annealing, polishing, or shot-peening. Once the material has been trained to exhibit the two-way shape-memory effect, the shape change between the low and high temperature states is generally reversible and persists through a high number of thermal cycles. In contrast, active materials that exhibit the extrinsic two-way shape-memory effects are composite or multi-component materials that combine a shape-memory alloy composition that exhibits a one-way effect with another element that provides a restoring force to reform the original shape.

The temperature at which the shape memory alloy remembers its high temperature form when heated is adjustable by slight changes in the composition of the alloy and through heat treatment. In nickel-titanium shape-memory alloys, for instance, it is changeable from above about 100° C. to below about −100° C. The shape recovery process occurs over a range of just a few degrees and the start or finish of the transformation is controllable to within a degree or two depending on the desired application and alloy composition. The mechanical properties of the shape-memory alloy vary greatly over the temperature range spanning their transformation, typically providing the system with shape memory effects, superelastic effects, and high damping capacity.

Depending on the type or intensity of the stimuli and also the desired response/function, some shape-memory materials may be composed of titanium, nickel, copper, aluminum, zirconium, niobium, cobalt, manganese, palladium, platinum, hafnium, gallium, gold, tantalum, iridium, ruthenium, uranium, and combinations thereof. The combination of two of these materials or other metals may also be used for shape-memory alloys. Some examples of suitable shape-memory alloy materials include, without limitation, nickel-titanium based alloys, indium-titanium based alloys, nickel-aluminum based alloys, nickel-gallium based alloys, copper based alloys (e.g., copper-zinc alloys, copper-aluminum alloys, copper-gold, and copper-tin alloys), gold-cadmium based alloys, silver-cadmium based alloys, indium-cadmium based alloys, manganese-copper based alloys, iron-platinum based alloys, iron-platinum based alloys, iron-palladium based alloys, and the like. The alloys can be binary, ternary, or any higher order so long as the alloy composition exhibits a shape memory effect, e.g., change in shape orientation, damping capacity, and the like. For example, in some implementations the shape-memory alloys may comprise a composite of three elements (e.g., titanium, nickel, and copper). The transformation point can be tuned by using different combinations of the elements or changing the concentration of each element in the composite.

In some cases, shape memory alloys exhibit a modulus increase of up to about 2.5 times and a dimensional change of up to about 8% (depending on the amount of pre-strain) when heated above their martensite to austenite phase transition temperature. Stress induced phase changes in shape memory alloys known as superelasticity (or pseudoelasticity) refer to the ability of shape-memory alloys to return to its original shape upon unloading after a substantial deformation in a two-way manner. Application of sufficient stress when shape-memory alloys are in their austenitic phase will cause them to change to their lower modulus Martensitic phase in which they can exhibit up to about 8% of superelastic deformation. Removal of the applied stress will cause the shape-memory alloys to switch back to their austenitic phase in so doing recovering their starting shape and higher modulus, and dissipating energy. More particularly, the application of an externally applied stress causes martensite to form at temperatures higher than $M_s$. The macroscopic deformation is accommodated by the formation of martensite. When the stress is released, the martensite phase transforms back into the austenite phase and the shape-memory alloys return back to their original shape. Superelastic shape memory alloys can be strained several times more than ordinary metal alloys without being permanently plastically deformed, however, this is only observed over a specific temperature range, with the largest ability to recover occurring close to $A_f$. Additional information regarding shape-memory alloys is provided in U.S. Pat. No. 9,316,212 to Browne et al., which is incorporated herein by reference in its entirety. See also Jani et al., *Materials & Design*, (1980-2015), Vol. 56, pages 1078-1113, and Borden, *Mechanical Engineering*, October 1991, pg. 67-72, which are incorporated herein by reference in their entireties. Additionally, example shape memory alloys are commercially available from DYNALLOY, Inc. of Irvine, Calif.

Shape memory polymers are similar to shape memory alloys in that they are capable of retaining two (or more) shapes induced by temperature; however, shape memory polymers may also change shape via an electric or magnetic field, exposure to light, change in pH level, or via a chemical reaction. In addition, while martensitic/austenitic transitions cause shape memory alloys to change shape, glass transition or melting transition cause shape memory polymers to change shape. Different types of polymers can be programmed to be used as shape memory polymers including acrylate compounds, polyester and copolyester compounds, block copolymers, polyurethanes and polyetheresters, polyketones, polyethylene, PMMA, Hydrogel, and elastomers. Various physical or chemical crosslinkers can be used for the above polymers. Some common chemical crosslinkers are acrylamide, dimethacrylate, etc. In one implementation, an example of a polymer composite material may comprise randomly distributing micro/nanoparticles (iron oxide, zinc oxide, etc.) in the bulk polymer and applying an electromagnetic field to energize the particles and elevate their temperature. The thermal energy may then be transferred from the particle into the bulk polymer causing it to alter shape.

In the depicted implementation, the shape-memory materials exhibit a two-way shape memory effect. For example, the actuating members 185A, 185B of the depicted implementation are configured to move to an extended, open shape in the presence of heat from the heating member 134, and a retracted, closed shape in the absence of heat from the heating member 134. Because the actuating members 185A, 185B cover the channels 191A, 192B of the base member 181, when the actuating members 185A, 185B are in the retracted position, there is little to no flow of the liquid composition through the channels 191A, 191B. When the actuating members 185A, 185B of the depicted implementation are in the extended position, however, flow of the liquid composition through the channels 191A, 191B is permitted. Moreover, given the arrangement of the actuating members 185A, 185B, base member 181, and the second liquid transport element 182, when the actuating members 185A, 185B of the depicted implementation are in the extended position, the liquid composition may flow into the second liquid transport element 182, such as by flowing through the channels 192A, 192B and into the second liquid transport element 182, for example, by flowing into the second liquid transport element 182 through the walls of the channels 192A, 192B.

As noted above, the actuating members 185A, 185B of the microvalve 182 are configured to exhibit a two-way shape memory effect based on the presence or absence of heat from the heating member 134. It should be noted that in other implementations, actuating members of a microvalve according to the present disclosure may exhibit shape memory effects based on one or more other external stimuli, including, for example, via pressure, stress, force, pH level, an electric or magnetic field, exposure to light, via a chemical reaction, etc.

In some implementations an inductive coil may be used to induce a magnetic field that may activate a microvalve of the present disclosure. In some implementations, for example, a hydrogel may be used as the microvalve. For example, some implementations may comprise a hybrid hydrogel-ferromagnetic material (for example, using $Fe_3O_4$ particles in a hydrogel). In such a manner, the hydrogel material may heat up by absorbing electromagnetic waves, which results in shrinkage or expansion of the hydrogel embedded in a channel, thus resulting in opening or closing of the channel to deliver an aerosol precursor composition. It should be noted that in some implementations, the inductive coil may have a dual purpose. For example, in some implementations the inductive coil may also provide heat to the aerosol precursor composition (such as, for example, via one or more susceptor components) for purposes of generating an aerosol.

In other implementations, a change in pH level may trigger the shape memory effects of a microvalve of the present disclosure. For example, in some implementations a small chamber filled with a pH-controlled solution may be included such that the chamber can be mechanically activated by a user pressing directly (or indirectly) on the chamber. In such a manner, when a user presses on the chamber, the increased pressure in the chamber delivers a small amount of the pH-controlled liquid through one or more micro channels to the vicinity of a microvalve (such as, for example, a hydrogel microvalve) to activate the microvalve. When the pressure is removed, the liquid returns to the small chamber.

Although in some implementations the actuating members may experience the presence or absence of heat directly from the heating member, in the depicted implementation the presence or absence of heat from the heating member 134 is experienced via a heat transport element 187. Although other configurations are possible, in the depicted implementation the heat transport element 187 comprises a central portion that includes an opening therethrough, and two leg portions that extend downward and approximately perpendicular therefrom. In the depicted implementation, a distal end of each leg portion is connected to a respective actuating member 185A, 185B. In various implementations, the heat transport element may comprise one or more conductive materials, including, for example, copper, aluminum, stainless steel, etc.

Figure 10:
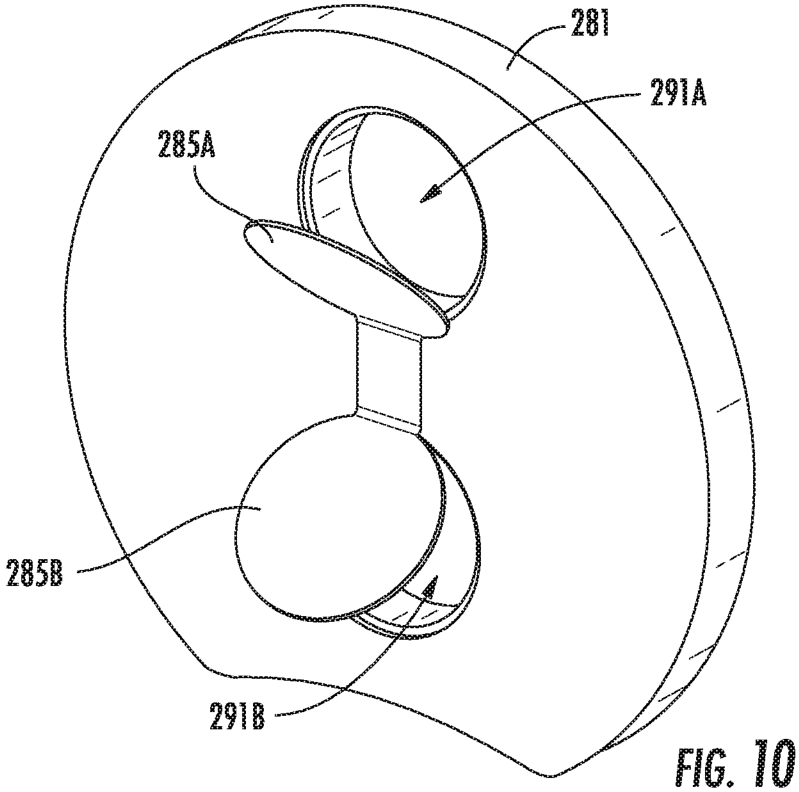
FIG. 10 illustrates a perspective view of a portion of a cartridge wherein the microvalve is shown in an open position, according to an example implementation of the present disclosure.
Figure 11:
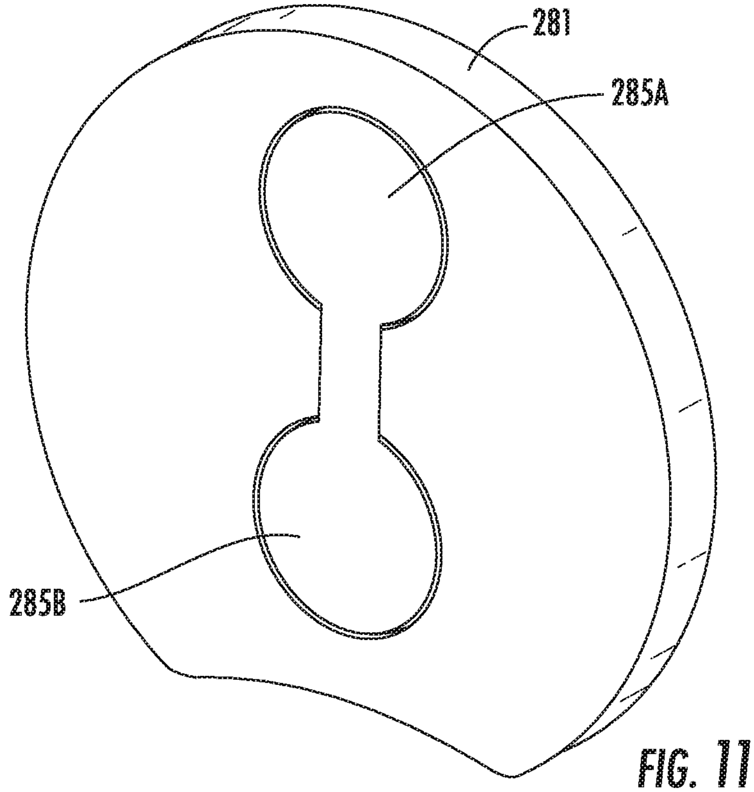
FIG. 11 illustrates a perspective view of a portion of a cartridge wherein the microvalve is shown in a closed position, according to an example implementation of the present disclosure.

FIGS. 10 and 11 illustrate perspective views of a portion a cartridge according to another example implementation of the present disclosure. In particular, FIG. 10 illustrates a perspective view of a portion of a cartridge shown in an open position, including a base member 281 and actuating members 285A, 285B of a microvalve, and FIG. 11 illustrates a perspective view of the portion of the cartridge of FIG. 10 shown in a closed position. In many aspects, the microvalve and cartridge of this implementation may have some similar configurations and may include some similar components (and some similar configuration and component variations) as those of the microvalve and cartridge of FIGS. 2-9B, which may not be repeated here. As such, reference is made to the pertinent discussions of these configurations and components (and configuration and component variations).

In the depicted implementation, the actuating members 285A, 285B have a substantially circular shape and are configured to move to a lifted (open) position in the presence of heat from a heating member (see FIG. 10). Conversely, in the absence of heat from the heating member, the actuating members 285A, 285B are configured to have a lowered (closed) position (see FIG. 11). As noted above, in other implementations these may be reversed such that the lifted position occurs in the absence of heat and the lowered position occurs in the presence of heat. In the lowered, closed position, the actuating members 285A, 285B of the depicted implementation substantially cover the respective channels 291A, 291B (which, in the depicted implementation, have a substantially cylindrical shape) formed through the thickness of the base member 281 such that fluid is substantially blocked from flowing therethrough. In the lifted open position, the actuating members 285A, 285B permit flow of the liquid composition through the respective channels 291A, 291B of the base member 281. Although other configurations are possible, in the depicted implementation, the actuating members 285A, 285B comprise opposite ends of a common component. In particular, the actuating members 285A, 285B of the depicted implementation are configured as substantially circular plates that are connected together by a narrower center portion. In the depicted implementation, the actuating members 285A, 285B comprise a shape memory material, which may include any one, or any combination, of the shape memory materials described above. In some implementations, the microvalve may include a heat transfer component that may be attached to the actuating members similar to the heat transfer component described above, although other implementations need not include a heat transfer component.

Figure 12:
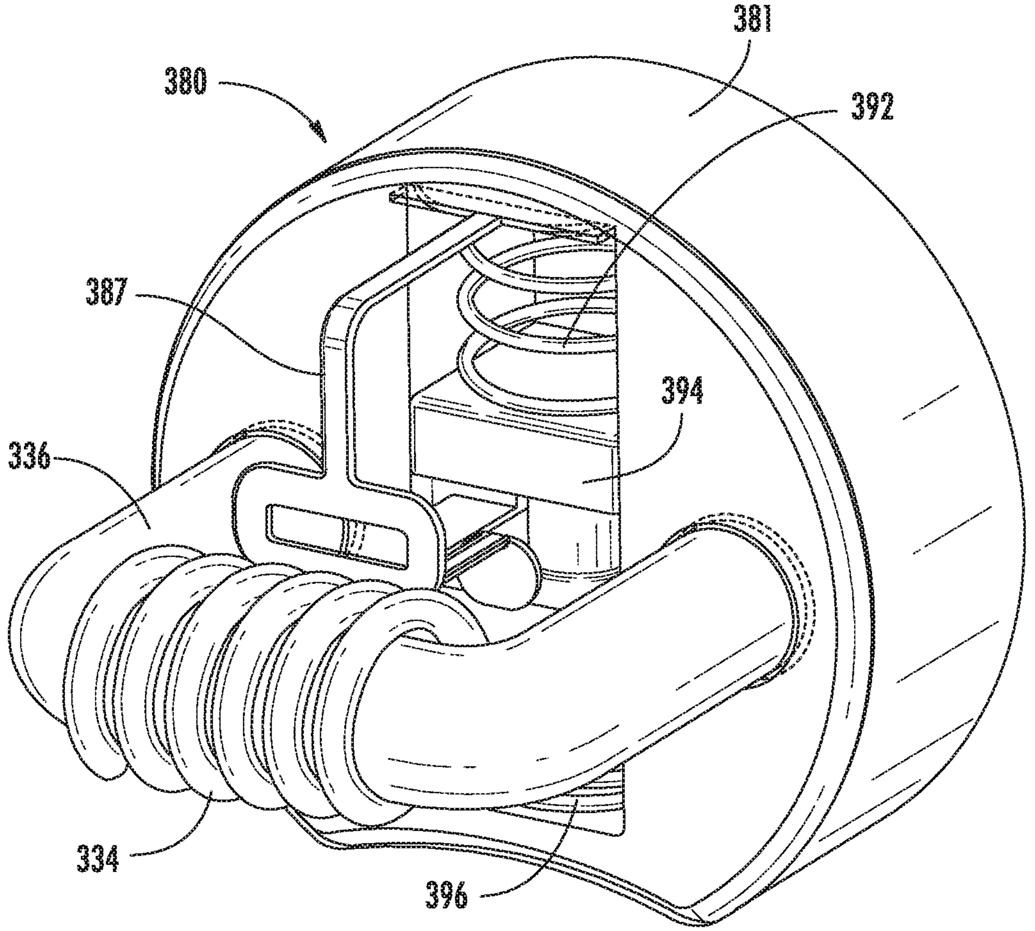
FIG. 12 illustrates a perspective view of a portion of a cartridge, according to an example implementation of the present disclosure.
Figure 13:
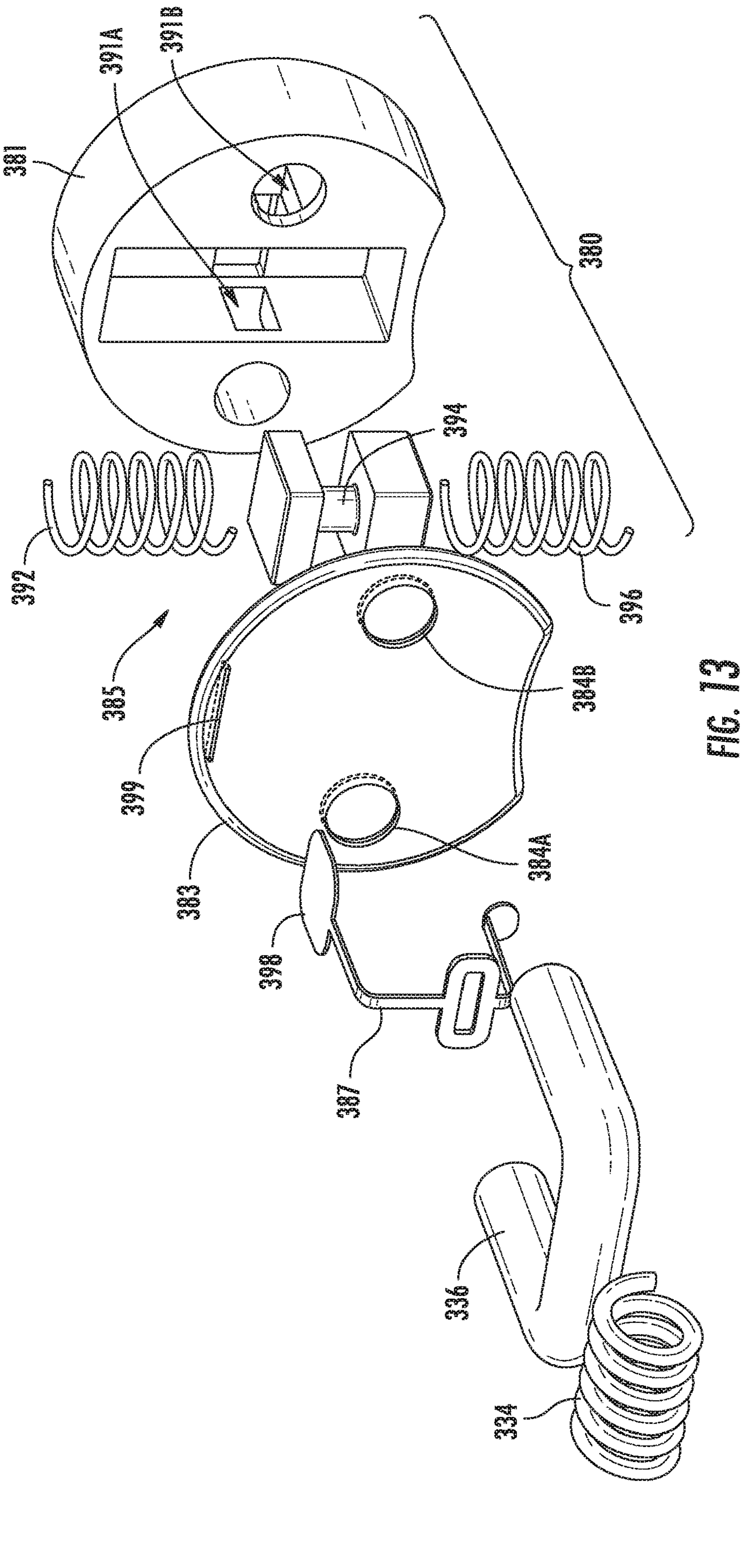
FIG. 13 illustrates an exploded perspective view of a portion of the cartridge of FIG. 12, according to an example implementation of the present disclosure.
Figure 14A:
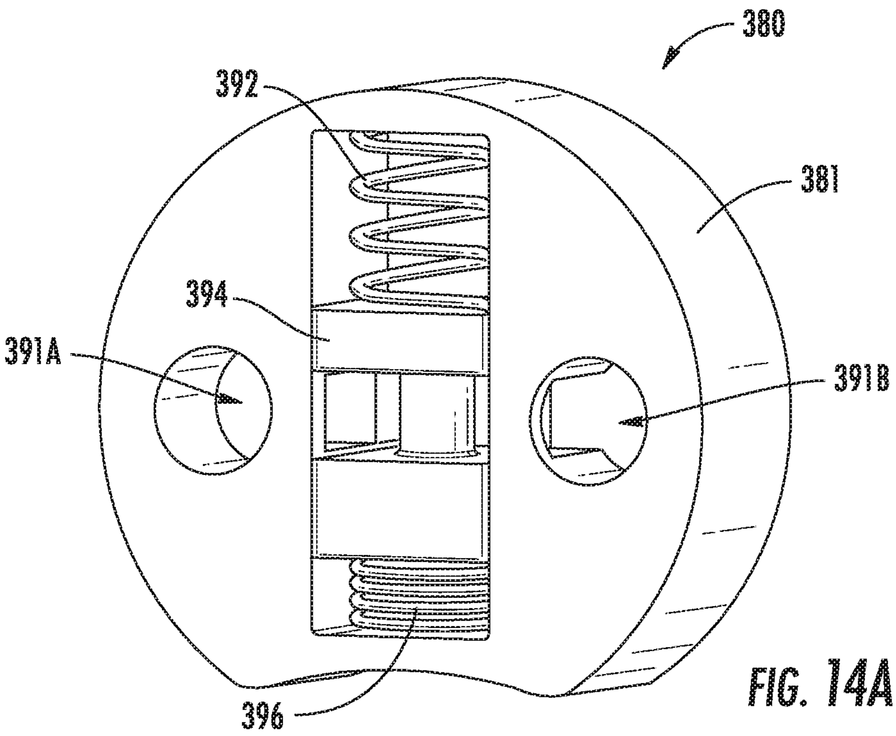
FIG. 14A illustrates a perspective view of a portion of the cartridge of FIG. 12 wherein the microvalve is shown in an open position, according to an example implementation of the present disclosure.
Figure 14B:
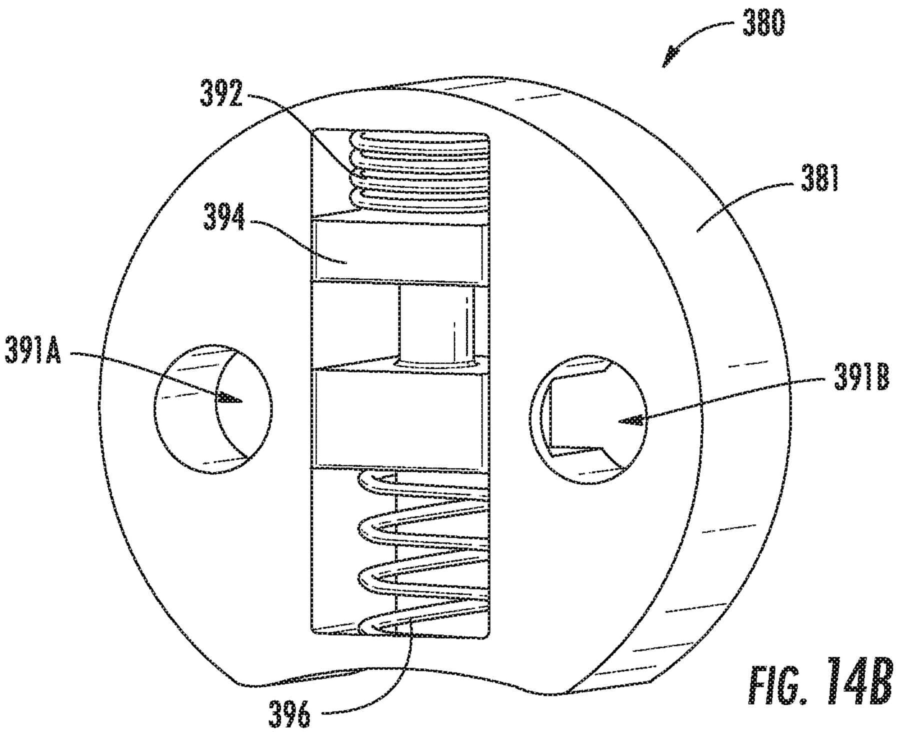
FIG. 14B illustrates a perspective view of a portion of the cartridge of FIG. 12 wherein the microvalve is shown in a closed position, according to an example implementation of the present disclosure.

FIGS. 12-14B illustrate a portion of a cartridge according to another example implementation of the present disclosure. In particular FIG. 12 illustrates a perspective view of a portion of a cartridge; FIG. 13 illustrates an exploded perspective view of the portion of the cartridge of FIG. 12; FIG. 14A illustrates a perspective view of the portion of the cartridge of FIG. 12 wherein the microvalve is in an open position; and FIG. 14B illustrates a perspective view of a portion of the cartridge of FIG. 12 wherein the microvalve is in a closed position. Referring to FIG. 12, the portion of the cartridge of the depicted implementation includes a heating member 334 (a portion of which is shown in the figure), a liquid transport element 336, and microvalve 380. Referring to FIG. 13, the microvalve 380 of the depicted implementation comprises a cover plate 383, a base member 381 that includes a pair of channels 391A, 391B, and an actuating member 385, which, as will be described in more detail below, is configured to move between open and closed positions (and vice versa). The depicted implementation also includes a heat transfer component 387 that is configured to transfer heat from the heating member 334 to the actuating member 385 wherein in the first position, the actuating member substantially blocks fluid flow from the liquid reservoir through the channel, and in the second position, the actuating member allows fluid flow from the liquid reservoir through the channel and to the liquid transport element. In various implementations, the heat transport element may comprise one or more conductive materials, including, for example, gold, silver, copper, aluminum, stainless steel, etc.

Referring to the figures, in the depicted implementation the liquid transport element 336 is adapted to wick or otherwise transport the liquid composition stored in a liquid reservoir to the heating member 334, which is disposed proximate the liquid transport element 336. For example, in the depicted implementation at least a portion of the heating member 334 comprises a wire coil that is configured to be wrapped around at least a portion of the liquid transport element 336. Although a variety of other configurations are possible, the liquid transport element 336 of the depicted implementation generally has a U-shape comprising a central portion and two leg portions that extend from opposite ends of the central portion. In the depicted implementation, at least a portion of the heating member 334 is configured to be wrapped around at least a portion of the central portion of the liquid transport element 336. As such, when the heating member 334 is activated, at least a portion of the liquid composition in the liquid transport element 336 may be vaporized.

In various implementations, the liquid transport element 336 may be formed of one or more materials configured for transport of a liquid, such as by capillary action. For example, in some implementations the first liquid transport element can be formed of, for example, fibrous materials (e.g., organic cotton, cellulose acetate, regenerated cellulose fabrics, glass fibers), porous ceramics (alumina, silica, zirconia, SiC, SiN, AlN, etc.), porous metals, porous carbon, graphite, porous glass, sintered glass beads, sintered ceramic beads, capillary tubes, porous polymers, or the like. The liquid transport element thus can be any material that contains an open pore network (i.e., a plurality of pores that are interconnected so that fluid may flow from one pore to another in a plurality of direction through the element). The pores can be nanopores, micropores, macropores or combinations thereof. As further discussed herein, some implementations of the present disclosure can particularly relate to the use of non-fibrous transport elements. As such, in some embodiments, fibrous transport elements can be expressly excluded. Alternatively, combinations of fibrous transport elements and non-fibrous transport elements may be utilized. In some embodiments, the first liquid transport element may be a substantially solid non-porous material, such as a polymer or dense ceramic or metals, configured to channel liquid through apertures or slots while not necessarily relying upon wicking through capillary action. Such a solid body may be used in combination with a porous absorptive pad. The absorptive pad can be formed of silica-based fibers, organic cotton, rayon fibers, cellulose acetate, regenerated cellulose fabrics, highly porous ceramic or metal mesh, etc.

As noted, in some implementations the liquid transport element may be formed partially or completely from a porous monolith, such as a porous ceramic, a porous glass, porous polymer, or the like. Some example monolithic materials that may be suitable for use according to implementations of the present disclosure are described, for example, in U.S. Pat. App. Pub. No. 2017/0188626 to Davis et al., and U.S. Pat. App. Pub. No. 2014/0123989 to LaMothe, the disclosures of which are incorporated herein by reference in their entireties. In some implementations the porous monolith may form a substantially rigid wick. In particular, the transport element can be substantially a single, monolithic material rather than a bundle of individual fibers as known in the art.

Various implementations of materials configured to produce heat when electrical current is applied therethrough may be employed to form the heating member 334. Example materials from which the wire coil may be formed include Kanthal (FeCrAl), nichrome, nickel, stainless steel, indium tin oxide, tungsten, molybdenum disilicide ($MoSi_2$), molybdenum silicide (MoSi), molybdenum disilicide doped with aluminum ($Mo(Si,Al)_2$), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics). In some implementations, the heating member 334 may be resistive heating element. In other implementations, the heating member may be configured to generate heat through induction. In some implementations, the heating member 334 may be coated by heat conductive ceramics such as aluminum nitride, silicon carbide, beryllium oxide, alumina, silicon nitride, or their composites.

In the depicted implementation, the legs of the U-shaped liquid transport element 336 are configured to extend into the channels 391A, 391B of the base member 381 through apertures 384A, 384B of the cover plate 383, which is configured to cover the base member 381 when in an assembled condition. In various implementations, the cover plate 383 may be constructed of a rigid material, such as a plastic, metal, or ceramic material, although other materials are possible. In the depicted implementation, the base member 381 may be constructed of porous material, or a substantially non-porous material, such as, for example, substantially non-porous polymeric, ceramic, or metal materials. In other implementations, the base member may comprise a low porosity material. In the case of a porous material, reference is made to the list of possible materials for the first or second liquid transport elements. For those implementations in which the base member is constructed of a porous material, when the actuating members are in the closed position, the base member may provide wicking through the base member. Consequently, the liquid composition may be absorbed into the liquid transport element through the channels of the base member (e.g., via a high wicking rate) and/or through the base member itself (e.g., via a low wicking rate).

As will be discussed in more detail below, the depicted implementation also includes a microvalve 380 that is configured to move between a first position and a second position (and vice versa) based on heat (or lack of heat) produced by the heating member 334. In various implementations, the first and second positions represent open and closed positions (or vice versa), wherein in the open position, fluid is permitted to flow from the liquid reservoir through the microvalve 380, and in the closed position, the microvalve substantially blocks fluid flow from the liquid reservoir.

In the depicted implementation, the base member 381 may comprise a porous material, or a substantially non-porous material, such as, for example, substantially non-porous polymeric, ceramic, or metal materials. In the case of a porous material, reference is made to the list of possible materials for the liquid transport element. For those implementations in which the base member comprises a porous material, when the actuating member is in the closed position, the base member may provide wicking through the base member. Consequently, the liquid composition may be absorbed into the second liquid transport element through the channels of the base member (e.g., via a high wicking rate) and/or through the base member itself (e.g., via a low wicking rate).

As noted above, the microvalve 380 includes the base member 381 and an actuating member 385. In the depicted implementation, the actuating member 385 comprises a spring and plunger mechanism. In particular, the actuating member 385 of the depicted implementation comprises a first spring 392, a second spring 396, and a plunger 394 disposed between the first spring 392 and the second spring 396. Although a variety of shapes are possible, the plunger 394 of the depicted implementation comprises a pair of wider end portions and a central narrower portion disposed between the wider end portions. In the depicted implementation, the plunger 394 is configured to move (via movement of the first spring 392 and/or the second spring 396) within a trough feature of the base member 381 between first and second positions (or vice versa), which may comprise closed and open positions (or vice versa). In the closed position, the first spring 392 and the second spring 396 position the plunger 394 such that the plunger 394 substantially blocks fluid flow from the liquid reservoir through the channels 391A, 391B. In the open position, the first spring 392 and the second spring 396 position the plunger 394 such that fluid may flow from the liquid reservoir through the channels 391A, 391B and to the liquid transport element 336.

In the depicted implementation, the first spring 392 comprises a shape-memory material, which may include any one, or any combination, of the shape memory materials described above. The second spring 396 of the depicted implementation comprises a metal material (e.g., a stainless steel material, a steel alloy material, a carbon steel material, a cobalt-nickel material, a copper alloy, a nickel alloy, a titanium material, etc.) and/or a plastic material (e.g., a polyethylene material, a polypropylene material, an acetal copolymer material, a linear polyphenylene sulfide material, a nylon material, an acrylonitrile butadiene styrene (ABS) material, a urethane material, an ethylene propylene diene monomer (EPDM) material, etc.). The plunger 394 of the depicted implementation may comprise a plastic or metal material, including any of the materials listed above. It should be noted that in other implementations, the second spring may be replaced with a different component that provides the force required to return the microvalve to its original position, such as, for example, various component with a resilient characteristics. For example, in some implementations the second spring may be replaced with a component made of a flexible material (such as, for example, an elastomeric material), which may have various shapes and/or forms.

The depicted implementation also includes a heat transfer component 387 that is configured to transfer heat from the heating member 334 to the first spring 392. Although in some implementations the actuating member may experience the presence or absence of heat directly from the heating member, in the depicted implementation the presence or absence of heat from the heating member 334 is experienced via the heat transport element 387. Although other configurations are possible, in the depicted implementation the heat transport element 387 comprises a central portion that includes an opening therethrough, and two leg portions that extend downward and approximately perpendicular therefrom. In the depicted implementation, a distal end of one of the leg portions includes a substantially flat contact feature 398 that is configured to contact one end of the first spring 392. In particular, the contact feature 398 is configured to extend through a slot 399 of the cover plate 383 such that it is located in the trough feature and contacts an end of the first spring 392.

Referring to FIGS. 14A and 14B, the shape-memory materials of the depicted implementation exhibit a two-way shape memory effect. For example, the first spring 392 of the depicted implementation is configured to move to an extended position in the presence of heat from the heating member (see FIG. 14A), and a retracted position in the absence of heat from the heating member (see FIG. 14B). In other implementations, however, these may be reversed such that the first spring may assume a retracted position in the presence of heat from the heating member and an extended position in the absence of heat from the heating member.

In the retracted position of the depicted implementation (see FIG. 14B), the second spring 396 biases the plunger 394 into the closed position, in which a portion of the plunger (e.g., one of the wider end portions) substantially blocks the channels 391A, 391B of the base member 381. Because a portion of the plunger 394 covers the channels 391A, 391B of the base member 381, there is little to no flow of the liquid composition through the channels 391A, 391B. When the first spring 392 of the depicted implementation is in the extended position (see FIG. 14A), however, a portion of the plunger (e.g., the central, narrower portion) is positioned proximate the channels 391A, 391B such that flow of the liquid composition through the channels 391A, 391B is permitted.

As noted above, the first spring 392 of the microvalve 380 is configured to exhibit a two-way shape memory effect based on the presence or absence of heat from the heating member 334. It should be noted that in other implementations, however, actuating members of a microvalve according to the present disclosure may exhibit shape memory effects based on one or more other external stimuli, including, for example, via pressure, stress, force, pH level, an electric or magnetic field, exposure to light, via a chemical reaction, etc.

Although in some implementations a cartridge and a control unit may be provided together as a complete aerosol delivery device generally, these components may be provided separately. For example, the present disclosure also encompasses a disposable unit for use with a reusable unit. In specific implementations, such a disposable unit (which may be a cartridge as illustrated in the appended figures) can be configured to engage a reusable unit (which may be a control unit as illustrated in the appended figures). In still other configurations, a cartridge may comprise a reusable unit and a control unit may comprise a disposable unit.

Although some figures described herein illustrate a cartridge and a control unit in a working relationship, it is understood that the cartridge and the control unit may exist as individual components. Accordingly, any discussion otherwise provided herein in relation to the components in combination also should be understood as applying to the control unit and the cartridge as individual and separate components.

In another aspect, the present disclosure may be directed to kits that provide a variety of components as described herein. For example, a kit may comprise a control unit with one or more cartridges. A kit may further comprise a control unit with one or more charging components. A kit may further comprise a control unit with one or more batteries. A kit may further comprise a control unit with one or more cartridges and one or more charging components and/or one or more batteries. In further implementations, a kit may comprise a plurality of cartridges. A kit may further comprise a plurality of cartridges and one or more batteries and/or one or more charging components. In the above implementations, the cartridges or the control units may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

It should be noted that the present disclosure contemplates other implementations of shape-memory material microvalves in addition to those described above. For example, in some implementations a responsive polymeric material may serve as a bladder configured to constrict (or expand) in response to stimulus in order to expel a controlled amount of liquid. Certain polymers under electro-stimulus may also be engineered to function as a sort of micro-pump to inject or release liquid into a target system. In addition, a flavor compound may be encapsulated by a responsive polymer, which may selectively open and close (e.g., pores of the polymer may appear and disappear) when exposed to a chemical or electromagnetic stimulus.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A cartridge for use in an aerosol delivery device, said cartridge comprising:

a housing defining a liquid reservoir configured to contain an aerosol precursor composition;

an atomizer configured to receive the aerosol precursor composition and to produce an aerosol, the atomizer comprising a first liquid transport element;

a second liquid transport element in fluid communication with the first liquid transport element; and a microvalve located between the liquid reservoir and the second liquid transport element, wherein the microvalve comprises a base member including at least one channel defined therethrough, and at least one actuating member at least a portion of which is constructed of a shape-memory material, and which is configured, in response to a stimulus, to move between a first position and a second position, wherein in the first position, the actuating member blocks fluid flow from the liquid reservoir through the channel, and in the second position, the actuating member allows fluid flow from the liquid reservoir through the channel and to the second liquid transport element, wherein the actuating member comprises an extending cup positioned proximate the channel.

2. The cartridge of claim 1, wherein the atomizer comprises a heating member, wherein at least a portion of the heating member is disposed proximate the first liquid transport element, and wherein the stimulus comprises heat generated by the heating member.

3. A cartridge for use in an aerosol delivery device, said cartridge comprising:

a housing defining a liquid reservoir configured to contain an aerosol precursor composition;

an atomizer configured to receive the aerosol precursor composition and to produce an aerosol, the atomizer comprising a first liquid transport element;

a second liquid transport element in fluid communication with the first liquid transport element; and a microvalve located between the liquid reservoir and the second liquid transport element, wherein the microvalve comprises a base member including at least one channel defined therethrough, and at least one actuating member at least a portion of which is constructed of a shape-memory material, and which is configured, in response to a stimulus, to move between a first position and a second position, wherein in the first position, the actuating member blocks fluid flow from the liquid reservoir through the channel, and in the second position, the actuating member allows fluid flow from the liquid reservoir through the channel and to the second liquid transport element, wherein the base member includes a pair of channels, and wherein in the first position, the actuating member blocks fluid flow from the liquid reservoir through the pair of channels, and in the second position, the actuating member allows fluid flow from the liquid reservoir through the pair of channels and to the second liquid transport element.

4. The cartridge of claim 3, wherein the actuating member comprises a lifting plate positioned proximate the pair of channels.

5. A cartridge for use in an aerosol delivery device, said cartridge comprising:

a housing defining a liquid reservoir configured to contain an aerosol precursor composition;

an atomizer configured to receive the aerosol precursor composition and to produce an aerosol, the atomizer comprising a first liquid transport element;

a second liquid transport element in fluid communication with the first liquid transport element; and a microvalve located between the liquid reservoir and the second liquid transport element, wherein the microvalve comprises a base member including at least one channel defined therethrough, and at least one actuating member at least a portion of which is constructed of a shape-memory material, and which is configured, in response to a stimulus, to move between a first position and a second position, wherein in the first position, the actuating member blocks fluid flow from the liquid reservoir through the channel, and in the second position, the actuating member allows fluid flow from the liquid reservoir through the channel and to the second liquid transport element, wherein the atomizer comprises a heating member, wherein at least a portion of the heating member is disposed proximate the first liquid transport element, and wherein the stimulus comprises heat generated by the heating member, further comprising a heat transfer component configured to transfer heat from the heating member to the actuating member.

6. The cartridge of claim 5, wherein one end of the heat transfer component is configured to contact the actuating member.

7. The cartridge of claim 1, wherein at least a portion of the actuating member is constructed of a shape-memory alloy material.

8. The cartridge of claim 1, wherein at least a portion of the actuating member is constructed of a shape-memory polymer material.

9. The cartridge of claim 1, wherein the base member of the microvalve is constructed of a non-porous material.

10. The cartridge of claim 1, wherein the base member of the microvalve is constructed of a material that is at least partially porous.

11. A cartridge for use in an aerosol delivery device, said cartridge comprising:

a housing defining a liquid reservoir configured to contain an aerosol precursor composition;

an atomizer configured to receive the aerosol precursor composition and to produce an aerosol, the atomizer comprising a liquid transport element; and a microvalve located between the liquid reservoir and the liquid transport element, wherein the microvalve comprises a base member including at least one channel defined therethrough, and at least one actuating member comprising a spring and plunger mechanism, wherein at least a portion of the actuating member comprises a shape-memory material, which is configured, in response to a stimulus, to move between a first position and a second position, wherein in the first position, the actuating member blocks fluid flow from the liquid reservoir through the channel, and in the second position, the actuating member allows fluid flow from the liquid reservoir through the channel and to the liquid transport element, wherein the base member includes a pair of channels, and wherein in the first position, the actuating member blocks fluid flow from the liquid reservoir through the pair of channels, and in the second position, the actuating member allows fluid flow from the liquid reservoir through the pair of channels and to the liquid transport element.

12. The cartridge of claim 11, wherein the atomizer comprises a heating member, wherein at least a portion of the heating member is disposed proximate the liquid transport element, and wherein the stimulus comprises heat generated by the heating member.

13. A cartridge for use in an aerosol delivery device, said cartridge comprising:

a housing defining a liquid reservoir configured to contain an aerosol precursor composition;

an atomizer configured to receive the aerosol precursor composition and to produce an aerosol, the atomizer comprising a liquid transport element; and a microvalve located between the liquid reservoir and the liquid transport element, wherein the microvalve comprises a base member including at least one channel defined therethrough, and at least one actuating member comprising a spring and plunger mechanism, wherein at least a portion of the actuating member comprises a shape-memory material, which is configured, in response to a stimulus, to move between a first position and a second position, wherein in the first position, the actuating member blocks fluid flow from the liquid reservoir through the channel, and in the second position, the actuating member allows fluid flow from the liquid reservoir through the channel and to the liquid transport element, wherein the atomizer comprises a heating member, wherein at least a portion of the heating member is disposed proximate the liquid transport element, and wherein the stimulus comprises heat generated by the heating member, further comprising a heat transfer component configured to transfer heat from the heating member to the actuating member.

14. The cartridge of claim 13, wherein one end of the heat transfer component is configured to contact the actuating member.

15. The cartridge of claim 11, wherein at least a portion of the actuating member comprises a shape-memory alloy material.

16. The cartridge of claim 11, wherein at least a portion of the actuating member comprises a shape-memory polymer material.

17. The cartridge of claim 11, wherein the base member of the microvalve comprises a non-porous material.

18. The cartridge of claim 11, wherein the base member of the microvalve comprises a material that is at least partially porous.

19. An aerosol delivery device comprising:

a control unit that includes a power source and a control component; and a cartridge comprising:

a housing defining a liquid reservoir configured to contain an aerosol precursor composition;

an atomizer configured to receive the aerosol precursor composition and to produce an aerosol, the atomizer comprising a first liquid transport element;

a second liquid transport element in fluid communication with the first liquid transport element; and a microvalve located between the liquid reservoir and the second liquid transport element, wherein the control unit is configured to generate the stimulus, wherein the microvalve comprises a base member including at least one channel defined therethrough, and at least one actuating member, at least a portion of which comprises a shape-memory material, and which is configured, in response to the stimulus, to move between a first position and a second position, wherein in the first position, the actuating member blocks fluid flow from the liquid reservoir through the channel, and in the second position, the actuating member allows fluid flow from the liquid reservoir through the channel and to the second liquid transport element, wherein the actuating member comprises an extending cup positioned proximate the channel.

20. The aerosol delivery device of claim 19, wherein the atomizer comprises a heating member, wherein at least a portion of the heating member is disposed proximate the liquid transport element, and wherein the stimulus comprises heat generated by the heating member.

21. An aerosol delivery device comprising:

a control unit that includes a power source and a control component; and a cartridge comprising:

a housing defining a liquid reservoir configured to contain an aerosol precursor composition;

an atomizer configured to receive the aerosol precursor composition and to produce an aerosol, the atomizer comprising a first liquid transport element;

a second liquid transport element in fluid communication with the first liquid transport element; and a microvalve located between the liquid reservoir and the second liquid transport element, wherein the control unit is configured to generate the stimulus, wherein the microvalve comprises a base member including at least one channel defined therethrough, and at least one actuating member, at least a portion of which comprises a shape-memory material, and which is configured, in response to the stimulus, to move between a first position and a second position, wherein in the first position, the actuating member blocks fluid flow from the liquid reservoir through the channel, and in the second position, the actuating member allows fluid flow from the liquid reservoir through the channel and to the second liquid transport element, wherein the base member includes a pair of channels, and wherein in the first position, the actuating member blocks fluid flow from the liquid reservoir through the pair of channels, and in the second position, the actuating member allows fluid flow from the liquid reservoir through the pair of channels.

22. The aerosol delivery device of claim 21, wherein the actuating member comprises a lifting plate positioned proximate the pair of channels.

23. An aerosol delivery device comprising:

a control unit that includes a power source and a control component; and a cartridge comprising:

a housing defining a liquid reservoir configured to contain an aerosol precursor composition;

an atomizer configured to receive the aerosol precursor composition and to produce an aerosol, the atomizer comprising a first liquid transport element;

a second liquid transport element in fluid communication with the first liquid transport element; and a microvalve located between the liquid reservoir and the second liquid transport element, wherein the control unit is configured to generate the stimulus, wherein the microvalve comprises a base member including at least one channel defined therethrough, and at least one actuating member, at least a portion of which comprises a shape-memory material, and which is configured, in response to the stimulus, to move between a first position and a second position, wherein in the first position, the actuating member blocks fluid flow from the liquid reservoir through the channel, and in the second position, the actuating member allows fluid flow from the liquid reservoir through the channel and to the second liquid transport element, wherein the atomizer comprises a heating member, wherein at least a portion of the heating member is disposed proximate the liquid transport element, and wherein the stimulus comprises heat generated by the heating member, wherein the cartridge further comprises a heat transfer component configured to transfer heat from the heating member to the actuating member.

24. The aerosol delivery device of claim 23, wherein one end of the heat transfer component is configured to contact the actuating member.

25. The aerosol delivery device of claim 19, wherein at least a portion of the actuating member comprises a shape-memory alloy material.

26. The aerosol delivery device of claim 19, wherein at least a portion of the actuating member comprises a shape-memory polymer material.

27. The aerosol delivery device of claim 19, wherein the base member comprises a non-porous material.

28. The cartridge of claim 19, wherein the base member comprises a material that is at least partially porous.

29. An aerosol delivery device comprising:

a control unit that includes a power source and a control component; and a cartridge comprising:

a housing defining a liquid reservoir configured to contain an aerosol precursor composition;

an atomizer configured to receive the aerosol precursor composition and to produce an aerosol, the atomizer comprising a liquid transport element; and a microvalve located between the liquid reservoir and the liquid transport element, wherein the microvalve comprises a base member including at least one channel defined therethrough, and an actuating member at least a portion of which comprises a shape-memory material and which is configured, in response to a stimulus, to move between a first position and a second position, wherein in the first position, the actuating member blocks fluid flow from the liquid reservoir through the channel, and in the second position, the actuating member allows fluid flow from the liquid reservoir through the channel and to the liquid transport element, and wherein the actuating member comprises a spring and plunger mechanism, wherein the base member includes a pair of channels, and wherein in the first position, the actuating member blocks fluid flow from the liquid reservoir through the pair of channels, and in the second position, the actuating member allows fluid flow from the liquid reservoir through the pair of channels.

30. The aerosol delivery device of claim 29, wherein the atomizer comprises a heating member, wherein at least a portion of the heating member is disposed proximate the liquid transport element, and wherein the stimulus comprises heat generated by the heating member.

31. An aerosol delivery device comprising:

a control unit that includes a power source and a control component; and a cartridge comprising:

a housing defining a liquid reservoir configured to contain an aerosol precursor composition;

an atomizer configured to receive the aerosol precursor composition and to produce an aerosol, the atomizer comprising a liquid transport element; and a microvalve located between the liquid reservoir and the liquid transport element, wherein the microvalve comprises a base member including at least one channel defined therethrough, and an actuating member at least a portion of which comprises a shape-memory material and which is configured, in response to a stimulus, to move between a first position and a second position, wherein in the first position, the actuating member blocks fluid flow from the liquid reservoir through the channel, and in the second position, the actuating member allows fluid flow from the liquid reservoir through the channel and to the liquid transport element, and wherein the actuating member comprises a spring and plunger mechanism, wherein the atomizer comprises a heating member, wherein at least a portion of the heating member is disposed proximate the liquid transport element, and wherein the stimulus comprises heat generated by the heating member, further comprising a heat transfer component configured to transfer heat from the heating member to the actuating member.

32. The aerosol delivery device of claim 31, wherein one end of the heat transfer component is configured to contact the actuating member.

33. The aerosol delivery device of claim 29, wherein at least a portion of the actuating member comprises a shape-memory alloy material.

34. The aerosol delivery device of claim 29, wherein at least a portion of the actuating member comprises a shape-memory polymer material.

35. The aerosol delivery device of claim 29, wherein the base member comprises a non-porous material.

36. The aerosol delivery device of claim 29, wherein the base member comprises a material that is at least partially porous.

* * * * *